United States Patent

Memmel et al.

(10) Patent No.: US 12,286,425 B2
(45) Date of Patent: Apr. 29, 2025

(54) HERBICIDALLY ACTIVE BICYCLIC BENZAMIDES

(71) Applicant: Bayer Aktiengesellschaft, Leverkusen (DE)

(72) Inventors: Frank Memmel, Guntersblum (DE); Ralf Braun, Ramberg (DE); Christian Waldraff, Bad Vilbel (DE); Isolde Haeuser-Hahn, Leverkusen (DE); Anu Bheemaiah Machettira, Frankfurt am Main (DE); Hansjoerg Dietrich, Liederbach am Taunus (DE); Elmar Gatzweiler, Bad Nauheim (DE); Christopher Hugh Rosinger, Hofheim (DE); Elisabeth Asmus, Hofheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1158 days.

(21) Appl. No.: 16/975,642

(22) PCT Filed: Feb. 20, 2019

(86) PCT No.: PCT/EP2019/054252
§ 371 (c)(1),
(2) Date: Aug. 25, 2020

(87) PCT Pub. No.: WO2019/166304
PCT Pub. Date: Sep. 6, 2019

(65) Prior Publication Data
US 2020/0404920 A1    Dec. 31, 2020

(30) Foreign Application Priority Data

Feb. 28, 2018   (EP) .................... 18159079

(51) Int. Cl.
C07D 411/12   (2006.01)
A01N 43/713   (2006.01)
C07D 407/12   (2006.01)
C07D 409/12   (2006.01)

(52) U.S. Cl.
CPC .......... C07D 411/12 (2013.01); A01N 43/713 (2013.01); C07D 407/12 (2013.01); C07D 409/12 (2013.01)

(58) Field of Classification Search
None
See application file for complete search history.

(56) References Cited

U.S. PATENT DOCUMENTS

| 8,481,749 B2 | 7/2013 | Braun et al. |
| 2015/0291570 A1 | 10/2015 | Kraus et al. |
| 2015/0322003 A1 | 11/2015 | Ford et al. |

FOREIGN PATENT DOCUMENTS

| EP | 918056 A1 * | 5/1999 | ............. A01N 43/32 |
| WO | 2012028579 A1 | 3/2012 | |
| WO | 2013076315 A2 | 5/2013 | |
| WO | 2014184073 A1 | 11/2014 | |

OTHER PUBLICATIONS

International Search Report for Application PCT/EP2019/054252 mailed May 7, 2019.

* cited by examiner

Primary Examiner — Bethany P Barham
Assistant Examiner — Barbara S Frazier

(57) ABSTRACT

Benzoylamides of the general formula (I) are described as herbicides.
In this formula (I),

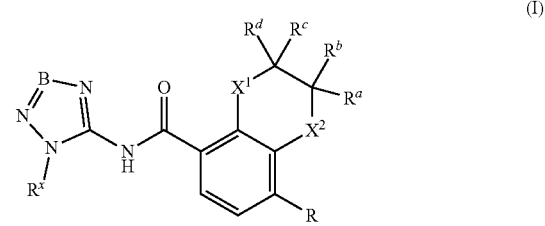

B, $X^1$ and $X^2$ represent N, O or $S(O)_n$, R, $R^a$, $R^b$, $R^c$, $R^d$ and IV represent radicals such as hydrogen, halogen, $(C_1$-$C_6)$-alkyl, $(C_1$-$C_6)$-alkyloxy and cyano.

9 Claims, No Drawings

HERBICIDALLY ACTIVE BICYCLIC BENZAMIDES

CROSS-REFERENCE TO RELATED APPLICATIONS

This application is the National Stage entry of International Application No. PCT/EP2019/054252, filed 20 Feb. 2019, which claims priority to European Patent Application No. 18159079.5, filed 28 Feb. 2018.

BACKGROUND

Field

The invention relates to the technical field of the herbicides, especially that of the herbicides for selective control of weeds and weed grasses in crops of useful plants.

Specifically, it relates to substituted bicyclic benzamides, to processes for their preparation and to their use as herbicides.

Description of Related Art

WO 2013/076315 A2 and WO 2014/184073 A1 each describe substituted N-(tetrazol-5-yl)- and N-(triazol-5-yl) arylcarboxamides fused in the 2,3- or preferably in the 3,4-position. The herbicidal activity of these known compounds, in particular at low application rates, and/or their compatibility with crop plants remain in need of improvement.

For the reasons stated, there is still a need for potent herbicides and/or plant growth regulators for the selective use in crop plants or the use on non-crop land, where these active ingredients preferably should have further advantageous properties in application, for example an improved compatibility with crop plants.

SUMMARY

Accordingly, it is an object of the present invention to provide compounds having herbicidal activity (herbicides) which are highly effective against economically important harmful plants even at relatively low application rates and can be used selectively in crop plants, preferably with good activity against harmful plants, and at the same time preferably have good compatibility with crop plants. Preferably, these herbicidal compounds should be particularly effective and efficient against a broad spectrum of weed grasses and preferably also have good activity against a large number of weeds.

Surprisingly it has now been found that the compounds of the formula (I) below and their salts have excellent herbicidal activity against a broad spectrum of economically important mono- and dicotyledonous annual harmful plants.

The present invention therefore provides compounds of the general formula (I)

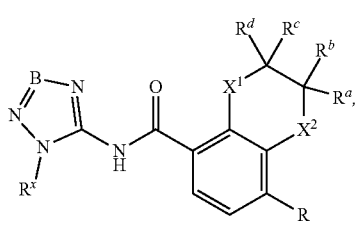

(I)

and their agrochemically acceptable salts, in which the symbols and indices have the following meanings:

B represents N or CH, $X^1$, $X^2$ independently of one another each represent O or $S(O)_n$, R represents halo-$(C_1$-$C_6)$-alkyl, $R^a$, $R^b$, $R^c$, $R^d$ independently of one another each represent hydrogen, fluorine, chlorine, hydroxy, $(C_1$-$C_6)$-alkyl, halo-$(C_1$-$C_6)$-alkyl, $(C_1$-$C_6)$-alkyloxy, $(C_1$-$C_6)$-alkylthio, cyano, or $R^a$ and $R^b$ or $R^c$ and $R^d$ together represent an oxo or a thiooxo group, $R^x$ represents $(C_1$-$C_6)$-alkyl, $(C_1$-$C_6)$-alkyl-O—$(C_1$-$C_6)$-alkyl, phenyl, n represents 0, 1 or 2.

DETAILED DESCRIPTION OF A PREFERRED EMBODIMENT

The compounds of the formula (I) are capable of forming salts. Salts may be formed by the action of a base on those compounds of the formula (I) that bear an acidic hydrogen atom. Suitable bases are, for example, organic amines such as trialkylamines, morpholine, piperidine or pyridine, and the hydroxides, carbonates and bicarbonates of ammonium, alkali metals or alkaline earth metals, especially sodium hydroxide, potassium hydroxide, sodium carbonate, potassium carbonate, sodium bicarbonate and potassium bicarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula [NRR'R''R''']$^+$ in which R to R''' each independently of one another represent an organic radical, in particular alkyl, aryl, aralkyl or alkylaryl. Also suitable are alkylsulfonium and alkylsulfoxonium salts, such as $(C_1$-$C_4)$-trialkylsulfonium and $(C_1$-$C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts comprise the conjugated base of the acid as the anion.

Suitable substituents present in deprotonated form, such as, for example, sulfonic acids or carboxylic acids, may form inner salts with groups which for their part can be protonated, such as amino groups.

Alkyl means saturated straight-chain or branched hydrocarbyl radicals having the number of carbon atoms specified in each case, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkoxy means saturated straight-chain or branched alkoxy radicals having the number of carbon atoms specified in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-1,2-difluoroethoxy, 2,2-dichloro-2-fluoroethoxy, 2,2,2-trichloroethoxy, pentafluoroethoxy and 1,1,1-trifluoroprop-2-oxy.

The term "halogen" means fluorine, chlorine, bromine or iodine. If the term is used for a radical, "halogen" means a fluorine, chlorine, bromine or iodine atom.

According to the nature of the substituents and the way in which they are joined, the compounds of the formula (I) may be present as stereoisomers. If, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries.

The invention also relates to all stereoisomers and mixtures thereof which are encompassed by the formula (I) but not defined specifically. However, the following text will, for the sake of simplicity, always mention compounds of the formula (I), even though this is understood as meaning not only the pure compounds, but also, if appropriate, mixtures with various amounts of isomeric compounds.

If a group is polysubstituted by radicals, this means that this group is substituted by one or more identical or different radicals from those mentioned.

In all the formulae specified hereinafter, the substituents and symbols have the same meaning as described in formula (I), unless defined differently. Arrows in a chemical formula denote the points at which it is joined to the rest of the molecule.

There follows a description of preferred, particularly preferred and very particularly preferred definitions of each of the individual substituents. The other substituents of the general formula (I) which are not specified hereinafter have the definition given above.

Preference is given to compounds of the general formula (I) where the symbols and indices have the following meanings:

B represents N or CH, $X^1$, $X^2$ independently of one another each represent O or $S(O)_n$, R represents halo-$(C_1$-$C_3)$-alkyl, $R^a$, $R^b$, $R^c$, $R^d$ independently of one another each represent hydrogen, fluorine, chlorine, hydroxy, $C_6$-alkyl, halo-$(C_1$-$C_6)$-alkyl, $(C_1$-$C_6)$-alkyloxy, $(C_1$-$C_6)$-alkylthio, cyano, or $R^a$ and $R^b$ or $R^c$ and $R^d$ together represent an oxo or a thiooxo group, $R^x$ represents $(C_1$-$C_3)$-alkyl, $(C_1$-$C_3)$-alkyl-O—$(C_1$-$C_3)$-alkyl, phenyl, n represents 0, 1 or 2.

Particular preference is given to compounds of the general formula (I) where the symbols and indices have the following meanings:

B represents N or CH, $X^1$, $X^2$ independently of one another each represent O or $S(O)_n$, R represents trifluoromethyl, difluoromethyl or pentafluoroethyl, $R^a$, $R^b$, $R^c$, $R^d$ independently of one another each represent hydrogen, fluorine, chlorine, hydroxy, methyl, ethyl, trifluoromethyl, difluoromethyl, methoxy, ethoxy, methylthio, ethylthio, cyano, or $R^a$ and $R^b$ or $R^c$ and $R^d$ together represent an oxo or a thiooxo group, $R^x$ represents methyl, ethyl, propyl, methoxymethyl, methoxyethyl, 2-methoxy-2-methyl-1-propyl, phenyl n represents 0, 1 or 2.

In the context of the present invention, the individual preferred and particularly preferred meanings of the substituents or indices B, $X^1$, $X^2$, R, $R^a$, $R^b$, $R^c$, $R^d$, $R^x$, $R^1$, $R^2$ and n can be combined with one another as desired.

This means that the present invention encompasses compounds of the general formula (I) in which, for example, the substituent $X^1$ has a preferred meaning and the substituents B, $X^2$, R, $R^a$, $R^b$, $R^c$, $R^d$, $R^x$, $R^1$ and $R^2$ and the index n have the general definition or else the substituent R has a preferred meaning, the substituent $R^a$ has a particularly preferred meaning and the remaining substituents have a general meaning.

Compounds of the formula (II) are likewise novel and are very well-suited as intermediates for the preparation of some of the compounds of the formula (I) according to the invention. The present invention therefore furthermore provides compounds of the formula (II)

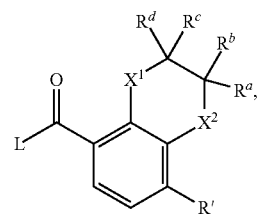

(II)

in which the symbols and indices have the following meanings:
L represents halogen or $R^3O$,
$R^3$ represents hydrogen or $(C_1-C_6)$-alkyl,
$X^1$, $X^2$ represent O or $S(O)_n$, where $X^1$ and $X^2$ are not simultaneously O or $S(O)_n$,
R' represents difluoromethyl, trifluoromethyl, 1,1,2,2-tetrafluoroethyl, pentafluoroethyl,
$R^a$, $R^b$, $R^c$, $R^d$ independently of one another each represent hydrogen, fluorine, chlorine, hydroxy, $(C_1-C_6)$-alkyl, halo-$(C_1-C_6)$-alkyl, $(C_1-C_6)$-alkyloxy, $(C_1-C_6)$-alkylthio, cyano, or
$R^a$ and $R^b$ or $R^c$ and $R^d$ together represent an oxo or a thiooxyl group,
n represents 0, 1 or 2.

Preference is given to compounds (II) in which the symbols and indices have the following meanings:

L represents chlorine, methoxy, ethoxy, hydroxy,
$X^1$, $X^2$ represent O or $S(O)_n$, where $X^1$ and $X^2$ are not simultaneously O or $S(O)_n$,
R' represents trifluoromethyl, difluoromethyl or pentafluoroethyl,
$R^a$, $R^b$, $R^c$, $R^d$ independently of one another each represent hydrogen, fluorine, chlorine, methyl, ethyl, trifluoromethyl, difluoromethyl, methoxy, ethoxy, methylthio, ethylthio, cyano, or
$R^a$ and $R^b$ or $R^c$ and $R^d$ together represent an oxo or a thiooxo group,
n represents 0, 1 or 2.

The compounds of the formula (I) according to the invention listed in tables 1 to 4 below and the compounds of the formula (I) according to the invention listed in tables 5 to 7 are very particularly preferred.

TABLE 1

Compounds of the general formula (I) in which B represents CH and $R^x$ represents methyl and $R^c$ and $R^d$ each represent hydrogen and the other substituents and indices have the meanings given below.

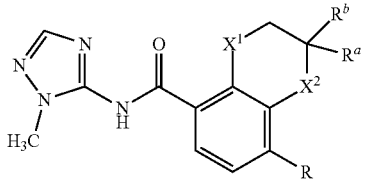

| No. | $X^1$ | $X^2$ | $R^a$ | $R^b$ | R |
|---|---|---|---|---|---|
| 1-1 | O | O | H | H | $CF_3$ |
| 1-2 | O | O | H | H | $CHF_2$ |
| 1-3 | O | O | F | F | $CF_3$ |
| 1-4 | O | O | F | F | $CHF_2$ |
| 1-5 | S | S | H | H | $CF_3$ |
| 1-6 | S | S | H | H | $CHF_2$ |
| 1-7 | S | S | F | F | $CF_3$ |
| 1-8 | S(O) | S(O) | H | H | $CF_3$ |
| 1-9 | S(O) | S(O) | H | H | $CHF_2$ |
| 1-10 | $SO_2$ | $SO_2$ | H | H | $CF_3$ |
| 1-11 | $SO_2$ | $SO_2$ | H | H | $CHF_2$ |
| 1-12 | O | S | H | H | $CF_3$ |
| 1-13 | O | S | H | H | $CHF_2$ |
| 1-14 | O | S | H | H | $CF_2CF_3$ |
| 1-15 | O | S(O) | H | H | $CF_3$ |
| 1-16 | O | S(O) | H | H | $CHF_2$ |
| 1-17 | O | S(O) | H | H | $CF_2CF_3$ |
| 1-18 | O | $SO_2$ | H | H | $CF_3$ |
| 1-19 | O | $SO_2$ | H | H | $CHF_2$ |
| 1-20 | O | $SO_2$ | H | H | $CF_2CF_3$ |
| 1-21 | O | S | Me | H | $CF_3$ |
| 1-22 | O | S | Me | H | $CHF_2$ |
| 1-23 | O | S(O) | Me | H | $CF_3$ |
| 1-24 | O | S(O) | Me | H | $CHF_2$ |
| 1-25 | O | $SO_2$ | Me | H | $CF_3$ |
| 1-26 | O | $SO_2$ | Me | H | $CHF_2$ |
| 1-27 | O | S | OMe | H | $CF_3$ |
| 1-28 | O | S | OMe | H | $CHF_2$ |
| 1-29 | O | S(O) | OMe | H | $CF_3$ |
| 1-30 | O | S(O) | OMe | H | $CHF_2$ |
| 1-31 | O | $SO_2$ | OMe | H | $CF_3$ |
| 1-32 | O | $SO_2$ | OMe | H | $CHF_2$ |
| 1-33 | O | S | OEt | H | $CF_3$ |
| 1-34 | O | S | OEt | H | $CHF_2$ |
| 1-35 | O | S(O) | OEt | H | $CF_3$ |
| 1-36 | O | S(O) | OEt | H | $CHF_2$ |
| 1-37 | O | $SO_2$ | OEt | H | $CF_3$ |
| 1-38 | O | $SO_2$ | OEt | H | $CHF_2$ |
| 1-39 | O | S | OH | H | $CF_3$ |
| 1-40 | O | S | OH | H | $CHF_2$ |
| 1-41 | O | S(O) | OH | H | $CF_3$ |
| 1-42 | O | S(O) | OH | H | $CHF_2$ |
| 1-43 | O | $SO_2$ | OH | H | $CF_3$ |

TABLE 1-continued

Compounds of the general formula (I) in which B represents CH and $R^x$ represents methyl and $R^c$ and $R^d$ each represent hydrogen and the other substituents and indices have the meanings given below.

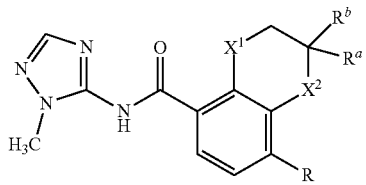

| No. | $X^1$ | $X^2$ | $R^a$ | $R^b$ | R |
|---|---|---|---|---|---|
| 1-44 | O | $SO_2$ | OH | H | $CHF_2$ |
| 1-45 | O | S | SMe | H | $CF_3$ |
| 1-46 | O | S | SMe | H | $CHF_2$ |
| 1-47 | O | S(O) | SMe | H | $CF_3$ |
| 1-48 | O | S(O) | SMe | H | $CHF_2$ |
| 1-49 | O | $SO_2$ | SMe | H | $CF_3$ |
| 1-50 | O | $SO_2$ | SMe | H | $CHF_2$ |
| 1-51 | O | S | CN | H | $CF_3$ |
| 1-52 | O | S | CN | H | $CHF_2$ |
| 1-53 | O | S(O) | CN | H | $CF_3$ |
| 1-54 | O | S(O) | CN | H | $CHF_2$ |
| 1-55 | O | $SO_2$ | CN | H | $CF_3$ |
| 1-56 | O | $SO_2$ | CN | H | $CHF_2$ |
| 1-57 | O | S | | C=O | $CF_3$ |
| 1-58 | O | S | | C=O | $CHF_2$ |
| 1-59 | O | S(O) | | C=O | $CF_3$ |
| 1-60 | O | S(O) | | C=O | $CHF_2$ |
| 1-61 | O | $SO_2$ | | C=O | $CF_3$ |
| 1-62 | O | $SO_2$ | | C=O | $CHF_2$ |
| 1-63 | O | S | | C=S | $CF_3$ |
| 1-64 | O | S | | C=S | $CHF_2$ |
| 1-65 | O | S(O) | | C=S | $CF_3$ |
| 1-66 | O | S(O) | | C=S | $CHF_2$ |
| 1-67 | O | $SO_2$ | | C=S | $CF_3$ |
| 1-68 | O | $SO_2$ | | C=S | $CHF_2$ |
| 1-69 | S | O | H | H | $CF_3$ |
| 1-70 | S | O | H | H | $CHF_2$ |
| 1-71 | S(O) | O | H | H | $CF_3$ |
| 1-72 | S(O) | O | H | H | $CHF_2$ |
| 1-73 | $SO_2$ | O | H | H | $CF_3$ |
| 1-74 | $SO_2$ | O | H | H | $CHF_2$ |

TABLE 2

Compounds of the general formula (I) in which B represents N and $R^x$ represents methyl and $R^c$ and $R^d$ each represent hydrogen and the other substituents and indices have the meanings given below.

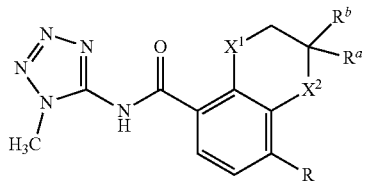

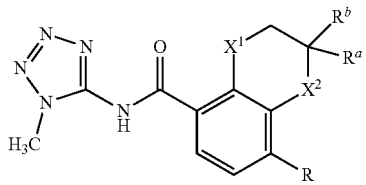

| No. | $X^1$ | $X^2$ | $R^a$ | $R^b$ | R |
|---|---|---|---|---|---|
| 2-1 | O | O | H | H | $CF_3$ |
| 2-2 | O | O | H | H | $CHF_2$ |
| 2-3 | O | O | F | F | $CF_3$ |
| 2-4 | O | O | F | F | $CHF_2$ |
| 2-5 | S | S | H | H | $CF_3$ |
| 2-6 | S | S | H | H | $CHF_2$ |
| 2-7 | S | S | F | F | $CF_3$ |
| 2-8 | S | S | F | F | $CHF_2$ |
| 2-9 | S(O) | S(O) | H | H | $CF_3$ |
| 2-10 | S(O) | S(O) | H | H | $CHF_2$ |
| 2-11 | $SO_2$ | $SO_2$ | H | H | $CF_3$ |
| 2-12 | $SO_2$ | $SO_2$ | H | H | $CHF_2$ |
| 2-13 | O | S | H | H | $CF_3$ |
| 2-14 | O | S | H | H | $CHF_2$ |
| 2-15 | O | S | H | H | $CF_2CF_3$ |
| 2-16 | O | S | OH | H | $CF_3$ |
| 2-17 | O | S(O) | H | H | $CF_3$ |
| 2-18 | O | S(O) | H | H | $CHF_2$ |
| 2-19 | O | S(O) | H | H | $CF_2CF_3$ |
| 2-20 | O | $SO_2$ | H | H | $CF_3$ |
| 2-21 | O | $SO_2$ | H | H | $CHF_2$ |
| 2-22 | O | $SO_2$ | H | H | $CF_2CF_3$ |

TABLE 2-continued

Compounds of the general formula (I) in which B represents N and $R^x$ represents methyl and $R^c$ and $R^d$ each represent hydrogen and the other substituents and indices have the meanings given below.

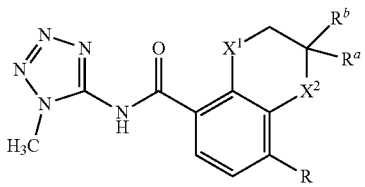

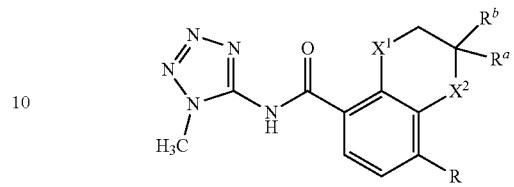

| No. | $X^1$ | $X^2$ | $R^a$ | $R^b$ | R |
|---|---|---|---|---|---|
| 2-23 | O | S | Me | H | $CF_3$ |
| 2-24 | O | S | Me | H | $CHF_2$ |
| 2-25 | O | S(O) | Me | H | $CF_3$ |
| 2-26 | O | S(O) | Me | H | $CHF_2$ |
| 2-27 | O | $SO_2$ | Me | H | $CF_3$ |
| 2-28 | O | $SO_2$ | Me | H | $CHF_2$ |
| 2-29 | O | S | OMe | H | $CF_3$ |
| 2-30 | O | S | OMe | H | $CHF_2$ |
| 2-31 | O | S(O) | OMe | H | $CF_3$ |
| 2-32 | O | S(O) | OMe | H | $CHF_2$ |
| 2-33 | O | $SO_2$ | OMe | H | $CF_3$ |
| 2-34 | O | $SO_2$ | OMe | H | $CHF_2$ |
| 2-35 | O | S | OEt | H | $CF_3$ |
| 2-36 | O | S | OEt | H | $CHF_2$ |
| 2-37 | O | S(O) | OEt | H | $CF_3$ |
| 2-38 | O | S(O) | OEt | H | $CHF_2$ |
| 2-39 | O | $SO_2$ | OEt | H | $CF_3$ |
| 2-40 | O | $SO_2$ | OEt | H | $CHF_2$ |
| 2-41 | O | S | Cl | H | $CF_3$ |
| 2-42 | O | S | Cl | H | $CHF_2$ |
| 2-43 | O | S(O) | Cl | H | $CF_3$ |
| 2-44 | O | S(O) | Cl | H | $CHF_2$ |
| 2-45 | O | $SO_2$ | Cl | H | $CF_3$ |
| 2-46 | O | $SO_2$ | Cl | H | $CHF_2$ |
| 2-47 | O | S | SMe | H | $CF_3$ |
| 2-48 | O | S | SMe | H | $CHF_2$ |
| 2-49 | O | S(O) | SMe | H | $CF_3$ |
| 2-50 | O | S(O) | SMe | H | $CHF_2$ |
| 2-51 | O | $SO_2$ | SMe | H | $CF_3$ |
| 2-52 | O | $SO_2$ | SMe | H | $CHF_2$ |
| 2-53 | O | S | CN | H | $CF_3$ |
| 2-54 | O | S | CN | H | $CHF_2$ |
| 2-55 | O | S(O) | CN | H | $CF_3$ |
| 2-56 | O | S(O) | CN | H | $CHF_2$ |
| 2-57 | O | $SO_2$ | CN | H | $CF_3$ |
| 2-58 | O | $SO_2$ | CN | H | $CHF_2$ |
| 2-59 | O | S | | C=O | $CF_3$ |
| 2-60 | O | S | | C=O | $CHF_2$ |
| 2-61 | O | S(O) | | C=O | $CF_3$ |
| 2-62 | O | S(O) | | C=O | $CHF_2$ |
| 2-63 | O | $SO_2$ | | C=O | $CF_3$ |
| 2-64 | O | $SO_2$ | | C=O | $CHF_2$ |
| 2-65 | O | S | | C=S | $CF_3$ |
| 2-66 | O | S | | C=S | $CHF_2$ |
| 2-67 | O | S(O) | | C=S | $CF_3$ |
| 2-68 | O | S(O) | | C=S | $CHF_2$ |
| 2-69 | O | $SO_2$ | | C=S | $CF_3$ |
| 2-70 | O | $SO_2$ | | C=S | $CHF_2$ |
| 2-71 | S | O | H | H | $CF_3$ |
| 2-72 | S | O | H | H | $CHF_2$ |
| 2-73 | S(O) | O | H | H | $CF_3$ |
| 2-74 | S(O) | O | H | H | $CHF_2$ |
| 2-75 | $SO_2$ | O | H | H | $CF_3$ |
| 2-76 | $SO_2$ | O | H | H | $CHF_2$ |

TABLE 3

Compounds of the general formula (I) in which B represents N and $R^x$ represents ethyl and $R^c$ and $R^d$ each represent hydrogen and the other substituents and indices have the meanings given below.

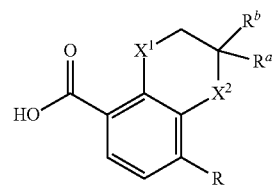

| No. | $X^1$ | $X^2$ | $R^a$ | $R^b$ | R |
|---|---|---|---|---|---|
| 3-1 | O | O | H | H | $CF_3$ |
| 3-2 | O | O | H | H | $CHF_2$ |
| 3-3 | O | O | F | F | $CF_3$ |
| 3-4 | O | O | F | F | $CHF_2$ |
| 3-5 | S | S | H | H | $CF_3$ |
| 3-6 | S | S | H | H | $CHF_2$ |
| 3-7 | S | S | F | F | $CF_3$ |
| 3-8 | S | S | F | F | $CHF_2$ |
| 3-9 | S(O) | S(O) | H | H | $CF_3$ |
| 3-10 | S(O) | S(O) | H | H | $CHF_2$ |
| 3-11 | $SO_2$ | $SO_2$ | H | H | $CF_3$ |
| 3-12 | $SO_2$ | $SO_2$ | H | H | $CHF_2$ |
| 3-13 | O | S | H | H | $CF_3$ |
| 3-14 | O | S | H | H | $CHF_2$ |
| 3-15 | O | S | H | H | $CF_2CF_3$ |
| 3-16 | O | S(O) | H | H | $CF_3$ |

TABLE 3-continued

Compounds of the general formula (I) in which B represents N and $R^x$ represents ethyl and $R^c$ and $R^d$ each represent hydrogen and the other substituents and indices have the meanings given below.

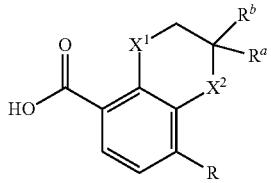

| No. | $X^1$ | $X^2$ | $R^a$ | $R^b$ | R |
|---|---|---|---|---|---|
| 3-17 | O | S(O) | H | H | $CHF_2$ |
| 3-18 | O | S(O) | H | H | $CF_2CF_3$ |
| 3-19 | O | $SO_2$ | H | H | $CF_3$ |
| 3-20 | O | $SO_2$ | H | H | $CHF_2$ |
| 3-21 | O | $SO_2$ | H | H | $CF_2CF_3$ |
| 3-22 | O | S | Me | H | $CF_3$ |
| 3-23 | O | S | Me | H | $CHF_2$ |
| 3-24 | O | S(O) | Me | H | $CF_3$ |
| 3-25 | O | S(O) | Me | H | $CHF_2$ |
| 3-26 | O | $SO_2$ | Me | H | $CF_3$ |
| 3-27 | O | $SO_2$ | Me | H | $CHF_2$ |
| 3-28 | O | S | OMe | H | $CF_3$ |
| 3-29 | O | S | OMe | H | $CHF_2$ |
| 3-30 | O | S(O) | OMe | H | $CF_3$ |
| 3-31 | O | S(O) | OMe | H | $CHF_2$ |
| 3-32 | O | $SO_2$ | OMe | H | $CF_3$ |
| 3-33 | O | $SO_2$ | OMe | H | $CHF_2$ |
| 3-34 | O | S | OEt | H | $CF_3$ |
| 3-35 | O | S | OEt | H | $CHF_2$ |
| 3-36 | O | S(O) | OEt | H | $CF_3$ |
| 3-37 | O | S(O) | OEt | H | $CHF_2$ |
| 3-38 | O | $SO_2$ | OEt | H | $CF_3$ |
| 3-39 | O | $SO_2$ | OEt | H | $CHF_2$ |
| 3-40 | O | S | OH | H | $CF_3$ |
| 3-41 | O | S | OH | H | $CHF_2$ |
| 3-42 | O | S(O) | OH | H | $CF_3$ |
| 3-43 | O | S(O) | OH | H | $CHF_2$ |
| 3-44 | O | $SO_2$ | OH | H | $CF_3$ |
| 3-45 | O | $SO_2$ | OH | H | $CHF_2$ |
| 3-46 | O | S | SMe | H | $CF_3$ |
| 3-47 | O | S | SMe | H | $CHF_2$ |
| 3-48 | O | S(O) | SMe | H | $CF_3$ |
| 3-49 | O | S(O) | SMe | H | $CHF_2$ |
| 3-50 | O | $SO_2$ | SMe | H | $CF_3$ |
| 3-51 | O | $SO_2$ | SMe | H | $CHF_2$ |
| 3-52 | O | S | CN | H | $CF_3$ |
| 3-53 | O | S | CN | H | $CHF_2$ |
| 3-54 | O | S(O) | CN | H | $CF_3$ |
| 3-55 | O | S(O) | CN | H | $CHF_2$ |
| 3-56 | O | $SO_2$ | CN | H | $CF_3$ |
| 3-57 | O | $SO_2$ | CN | H | $CHF_2$ |
| 3-58 | O | S | | C=O | $CF_3$ |
| 3-59 | O | S | | C=O | $CHF_2$ |
| 3-60 | O | S(O) | | C=O | $CF_3$ |
| 3-61 | O | S(O) | | C=O | $CHF_2$ |
| 3-62 | O | $SO_2$ | | C=O | $CF_3$ |
| 3-63 | O | $SO_2$ | | C=O | $CHF_2$ |
| 3-64 | O | S | | C=S | $CF_3$ |
| 3-65 | O | S | | C=S | $CHF_2$ |
| 3-66 | O | S(O) | | C=S | $CF_3$ |
| 3-67 | O | S(O) | | C=S | $CHF_2$ |
| 3-68 | O | $SO_2$ | | C=S | $CF_3$ |
| 3-69 | O | $SO_2$ | | C=S | $CHF_2$ |
| 3-70 | S | O | H | H | $CF_3$ |
| 3-71 | S | O | H | H | $CHF_2$ |
| 3-72 | S(O) | O | H | H | $CF_3$ |
| 3-73 | S(O) | O | H | H | $CHF_2$ |
| 3-74 | $SO_2$ | O | H | H | $CF_3$ |
| 3-75 | $SO_2$ | O | H | H | $CHF_2$ |

TABLE 4

Compounds of the general formula (I) in which B represents CH and $R^x$ represents propyl and $R^c$ and $R^d$ each represent hydrogen and the other substituents and indices have the meanings given below.

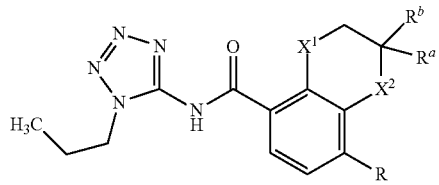

| No. | $X^1$ | $X^2$ | $R^a$ | $R^b$ | R |
|---|---|---|---|---|---|
| 4-1 | O | O | H | H | $CF_3$ |
| 4-2 | O | O | H | H | $CHF_2$ |
| 4-3 | O | O | F | F | $CF_3$ |
| 4-4 | O | O | F | F | $CHF_2$ |
| 4-5 | S | S | H | H | $CF_3$ |
| 4-6 | S | S | H | H | $CHF_2$ |
| 4-7 | S | S | F | F | $CF_3$ |
| 4-8 | S(O) | S(O) | H | H | $CF_3$ |
| 4-9 | S(O) | S(O) | H | H | $CHF_2$ |
| 4-10 | $SO_2$ | $SO_2$ | H | H | $CF_3$ |
| 4-11 | $SO_2$ | $SO_2$ | H | H | $CHF_2$ |
| 4-12 | O | S | H | H | $CF_3$ |
| 4-13 | O | S | H | H | $CHF_2$ |
| 4-14 | O | S | H | H | $CF_2CF_3$ |
| 4-15 | O | S(O) | H | H | $CF_3$ |
| 4-16 | O | S(O) | H | H | $CHF_2$ |
| 4-17 | O | S(O) | H | H | $CF_2CF_3$ |
| 4-18 | O | $SO_2$ | H | H | $CF_3$ |
| 4-19 | O | $SO_2$ | H | H | $CHF_2$ |
| 4-20 | O | $SO_2$ | H | H | $CF_2CF_3$ |
| 4-21 | O | S | Me | H | $CF_3$ |
| 4-22 | O | S | Me | H | $CHF_2$ |
| 4-23 | O | S(O) | Me | H | $CF_3$ |
| 4-24 | O | S(O) | Me | H | $CHF_2$ |
| 4-25 | O | $SO_2$ | Me | H | $CF_3$ |
| 4-26 | O | $SO_2$ | Me | H | $CHF_2$ |
| 4-27 | O | S | OMe | H | $CF_3$ |
| 4-28 | O | S | OMe | H | $CHF_2$ |
| 4-29 | O | S(O) | OMe | H | $CF_3$ |
| 4-30 | O | S(O) | OMe | H | $CHF_2$ |
| 4-31 | O | $SO_2$ | OMe | H | $CF_3$ |
| 4-32 | O | $SO_2$ | OMe | H | $CHF_2$ |
| 4-33 | O | S | OEt | H | $CF_3$ |
| 4-34 | O | S | OEt | H | $CHF_2$ |
| 4-35 | O | S(O) | OEt | H | $CF_3$ |
| 4-36 | O | S(O) | OEt | H | $CHF_2$ |
| 4-37 | O | $SO_2$ | OEt | H | $CF_3$ |
| 4-38 | O | $SO_2$ | OEt | H | $CHF_2$ |
| 4-39 | O | S | OH | H | $CF_3$ |
| 4-40 | O | S | OH | H | $CHF_2$ |
| 4-41 | O | S(O) | OH | H | $CF_3$ |
| 4-42 | O | S(O) | OH | H | $CHF_2$ |
| 4-43 | O | $SO_2$ | OH | H | $CF_3$ |
| 4-44 | O | $SO_2$ | OH | H | $CHF_2$ |
| 4-45 | O | S | SMe | H | $CF_3$ |
| 4-46 | O | S | SMe | H | $CHF_2$ |
| 4-47 | O | S(O) | SMe | H | $CF_3$ |
| 4-48 | O | S(O) | SMe | H | $CHF_2$ |
| 4-49 | O | $SO_2$ | SMe | H | $CF_3$ |
| 4-50 | O | $SO_2$ | SMe | H | $CHF_2$ |
| 4-51 | O | S | CN | H | $CF_3$ |
| 4-52 | O | S | CN | H | $CHF_2$ |
| 4-53 | O | S(O) | CN | H | $CF_3$ |
| 4-54 | O | S(O) | CN | H | $CHF_2$ |
| 4-55 | O | $SO_2$ | CN | H | $CF_3$ |
| 4-56 | O | $SO_2$ | CN | H | $CHF_2$ |
| 4-57 | O | S | | C=O | $CF_3$ |
| 4-58 | O | S | | C=O | $CHF_2$ |
| 4-59 | O | S(O) | | C=O | $CF_3$ |
| 4-60 | O | S(O) | | C=O | $CHF_2$ |
| 4-61 | O | $SO_2$ | | C=O | $CF_3$ |
| 4-62 | O | $SO_2$ | | C=O | $CHF_2$ |
| 4-63 | O | S | | C=S | $CF_3$ |
| 4-64 | O | S | | C=S | $CHF_2$ |
| 4-65 | O | S(O) | | C=S | $CF_3$ |

TABLE 4-continued

Compounds of the general formula (I) in which B represents CH and $R^x$ represents propyl and $R^c$ and $R^d$ each represent hydrogen and the other substituents and indices have the meanings given below.

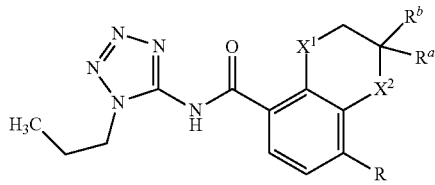

| No. | $X^1$ | $X^2$ | $R^a$ | $R^b$ | R |
| --- | --- | --- | --- | --- | --- |
| 4-66 | O | S(O) | | C=S | $CHF_2$ |
| 4-67 | O | $SO_2$ | | C=S | $CF_3$ |
| 4-68 | O | $SO_2$ | | C=S | $CHF_2$ |
| 4-69 | S | O | H | H | $CF_3$ |
| 4-70 | S | O | H | H | $CHF_2$ |
| 4-71 | S(O) | O | H | H | $CF_3$ |
| 4-72 | S(O) | O | H | H | $CHF_2$ |
| 4-73 | $SO_2$ | O | H | H | $CF_3$ |
| 4-74 | $SO_2$ | O | H | H | $CHF_2$ |

TABLE 5

Compounds of the general formula (II) in which L represents methoxy and $R^c$ and $R^d$ each represent hydrogen and the other substituents and indices have the meanings given below.

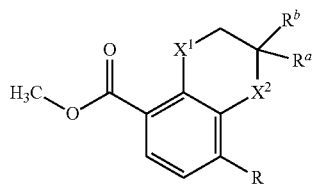

| No. | $X^1$ | $X^2$ | $R^a$ | $R^b$ | R' |
| --- | --- | --- | --- | --- | --- |
| 5-1 | O | S | H | H | $CF_3$ |
| 5-2 | O | S | H | H | $CHF_2$ |
| 5-3 | O | S | H | H | $CF_2CF_3$ |
| 5-4 | O | S(O) | H | H | $CF_3$ |
| 5-5 | O | S(O) | H | H | $CHF_2$ |
| 5-6 | O | S(O) | H | H | $CF_2CF_3$ |
| 5-7 | O | $SO_2$ | H | H | $CF_3$ |
| 5-8 | O | $SO_2$ | H | H | $CHF_2$ |
| 5-9 | O | $SO_2$ | H | H | $CF_2CF_3$ |
| 5-10 | O | S | Me | H | $CF_3$ |
| 5-11 | O | S | Me | H | $CHF_2$ |
| 5-12 | O | S(O) | Me | H | $CF_3$ |
| 5-13 | O | S(O) | Me | H | $CHF_2$ |
| 5-14 | O | $SO_2$ | Me | H | $CF_3$ |
| 5-15 | O | $SO_2$ | Me | H | $CHF_2$ |
| 5-16 | O | S | OMe | H | $CF_3$ |
| 5-17 | O | S | OMe | H | $CHF_2$ |
| 5-18 | O | S(O) | OMe | H | $CF_3$ |
| 5-19 | O | S(O) | OMe | H | $CHF_2$ |
| 5-20 | O | $SO_2$ | OMe | H | $CF_3$ |
| 5-21 | O | $SO_2$ | OMe | H | $CHF_2$ |
| 5-22 | O | S | OEt | H | $CF_3$ |
| 5-23 | O | S | OEt | H | $CHF_2$ |
| 5-24 | O | S(O) | OEt | H | $CF_3$ |
| 5-25 | O | S(O) | OEt | H | $CHF_2$ |
| 5-26 | O | $SO_2$ | OEt | H | $CF_3$ |
| 5-27 | O | $SO_2$ | OEt | H | $CHF_2$ |
| 5-28 | O | S | OH | H | $CF_3$ |
| 5-29 | O | S | OH | H | $CHF_2$ |
| 5-30 | O | S(O) | OH | H | $CF_3$ |
| 5-31 | O | S(O) | OH | H | $CHF_2$ |
| 5-32 | O | $SO_2$ | OH | H | $CF_3$ |
| 5-33 | O | $SO_2$ | OH | H | $CHF_2$ |
| 5-34 | O | S | SMe | H | $CF_3$ |
| 5-35 | O | S | SMe | H | $CHF_2$ |
| 5-36 | O | S(O) | SMe | H | $CF_3$ |

TABLE 5-continued

Compounds of the general formula (II) in which L represents methoxy and $R^c$ and $R^d$ each represent hydrogen and the other substituents and indices have the meanings given below.

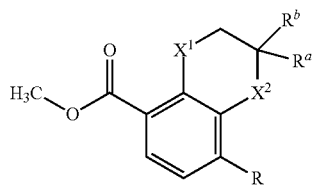

| No. | $X^1$ | $X^2$ | $R^a$ | $R^b$ | R' |
|---|---|---|---|---|---|
| 5-37 | O | S(O) | SMe | H | $CHF_2$ |
| 5-38 | O | $SO_2$ | SMe | H | $CF_3$ |
| 5-39 | O | $SO_2$ | SMe | H | $CHF_2$ |
| 5-40 | O | S | CN | H | $CF_3$ |
| 5-41 | O | S | CN | H | $CHF_2$ |
| 5-42 | O | S(O) | CN | H | $CF_3$ |
| 5-43 | O | S(O) | CN | H | $CHF_2$ |
| 5-44 | O | $SO_2$ | CN | H | $CF_3$ |
| 5-45 | O | $SO_2$ | CN | H | $CHF_2$ |
| 5-46 | O | S | | C=O | $CF_3$ |
| 5-47 | O | S | | C=O | $CHF_2$ |
| 5-48 | O | S(O) | | C=O | $CF_3$ |
| 5-49 | O | S(O) | | C=O | $CHF_2$ |
| 5-50 | O | $SO_2$ | | C=O | $CF_3$ |
| 5-51 | O | $SO_2$ | | C=O | $CHF_2$ |
| 5-52 | O | S | | C=S | $CF_3$ |
| 5-53 | O | S | | C=S | $CHF_2$ |
| 5-54 | O | S(O) | | C=S | $CF_3$ |
| 5-55 | O | S(O) | | C=S | $CHF_2$ |
| 5-56 | O | $SO_2$ | | C=S | $CF_3$ |
| 5-57 | O | $SO_2$ | | C=S | $CHF_2$ |
| 5-58 | S | O | H | H | $CF_3$ |
| 5-59 | S | O | H | H | $CHF_2$ |
| 5-60 | S(O) | O | H | H | $CF_3$ |
| 5-61 | S(O) | O | H | H | $CHF_2$ |
| 5-62 | $SO_2$ | O | H | H | $CF_3$ |
| 5-63 | $SO_2$ | O | H | H | $CHF_2$ |
| 5-64 | S | S | H | H | $CF_3$ |

TABLE 6

Compounds of the general formula (II) in which L represents hydroxy and $R^c$ and $R^d$ each represent hydrogen and the other substituents and indices have the meanings given below.

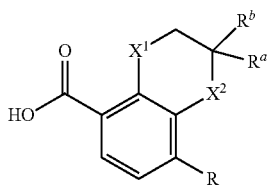

| No. | $X^1$ | $X^2$ | $R^a$ | $R^b$ | R' |
|---|---|---|---|---|---|
| 6-1 | O | S | H | H | $CF_3$ |
| 6-2 | O | S | H | H | $CHF_2$ |
| 6-3 | O | S | H | H | $CF_2CF_3$ |
| 6-4 | O | S(O) | H | H | $CF_3$ |
| 6-5 | O | S(O) | H | H | $CHF_2$ |
| 6-6 | O | S(O) | H | H | $CF_2CF_3$ |
| 6-7 | O | $SO_2$ | H | H | $CF_3$ |
| 6-8 | O | $SO_2$ | H | H | $CHF_2$ |
| 6-9 | O | $SO_2$ | H | H | $CF_2CF_3$ |
| 6-10 | O | S | Me | H | $CF_3$ |
| 6-11 | O | S | Me | H | $CHF_2$ |
| 6-12 | O | S(O) | Me | H | $CF_3$ |
| 6-13 | O | S(O) | Me | H | $CHF_2$ |
| 6-14 | O | $SO_2$ | Me | H | $CF_3$ |
| 6-15 | O | $SO_2$ | Me | H | $CHF_2$ |
| 6-16 | O | S | OMe | H | $CF_3$ |
| 6-17 | O | S | OMe | H | $CHF_2$ |

TABLE 6-continued

Compounds of the general formula (II) in which L represents hydroxy and $R^c$ and $R^d$ each represent hydrogen and the other substituents and indices have the meanings given below.

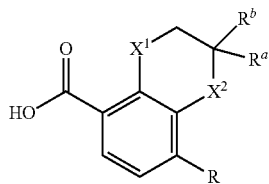

| No. | $X^1$ | $X^2$ | $R^a$ | $R^b$ | R' |
|---|---|---|---|---|---|
| 6-18 | O | S(O) | OMe | H | $CF_3$ |
| 6-19 | O | S(O) | OMe | H | $CHF_2$ |
| 6-20 | O | $SO_2$ | OMe | H | $CF_3$ |
| 6-21 | O | $SO_2$ | OMe | H | $CHF_2$ |
| 6-22 | O | S | OEt | H | $CF_3$ |
| 6-23 | O | S | OEt | H | $CHF_2$ |
| 6-24 | O | S(O) | OEt | H | $CF_3$ |
| 6-25 | O | S(O) | OEt | H | $CHF_2$ |
| 6-26 | O | $SO_2$ | OEt | H | $CF_3$ |
| 6-27 | O | $SO_2$ | OEt | H | $CHF_2$ |
| 6-28 | O | S | OH | H | $CF_3$ |
| 6-29 | O | S | OH | H | $CHF_2$ |
| 6-30 | O | S(O) | OH | H | $CF_3$ |
| 6-31 | O | S(O) | OH | H | $CHF_2$ |
| 6-32 | O | $SO_2$ | OH | H | $CF_3$ |
| 6-33 | O | $SO_2$ | OH | H | $CHF_2$ |
| 6-34 | O | S | SMe | H | $CF_3$ |
| 6-35 | O | S | SMe | H | $CHF_2$ |
| 6-36 | O | S(O) | SMe | H | $CF_3$ |
| 6-37 | O | S(O) | SMe | H | $CHF_2$ |
| 6-38 | O | $SO_2$ | SMe | H | $CF_3$ |
| 6-39 | O | $SO_2$ | SMe | H | $CHF_2$ |
| 6-40 | O | S | CN | H | $CF_3$ |
| 6-41 | O | S | CN | H | $CHF_2$ |
| 6-42 | O | S(O) | CN | H | $CF_3$ |
| 6-43 | O | S(O) | CN | H | $CHF_2$ |
| 6-44 | O | $SO_2$ | CN | H | $CF_3$ |
| 6-45 | O | $SO_2$ | CN | H | $CHF_2$ |
| 6-46 | O | S | | C=O | $CF_3$ |
| 6-47 | O | S | | C=O | $CHF_2$ |
| 6-48 | O | S(O) | | C=O | $CF_3$ |
| 6-49 | O | S(O) | | C=O | $CHF_2$ |
| 6-50 | O | $SO_2$ | | C=O | $CF_3$ |
| 6-51 | O | $SO_2$ | | C=O | $CHF_2$ |
| 6-52 | O | S | | C=S | $CF_3$ |
| 6-53 | O | S | | C=S | $CHF_2$ |
| 6-54 | O | S(O) | | C=S | $CF_3$ |
| 6-55 | O | S(O) | | C=S | $CHF_2$ |
| 6-56 | O | $SO_2$ | | C=S | $CF_3$ |
| 6-57 | O | $SO_2$ | | C=S | $CHF_2$ |
| 6-58 | S | O | H | H | $CF_3$ |
| 6-59 | S | O | H | H | $CHF_2$ |
| 6-60 | S(O) | O | H | H | $CF_3$ |
| 6-61 | S(O) | O | H | H | $CHF_2$ |
| 6-62 | $SO_2$ | O | H | H | $CF_3$ |
| 6-63 | $SO_2$ | O | H | H | $CHF_2$ |
| 6-64 | S | S | H | H | $CF_3$ |

TABLE 7

Compounds of the general formula (II) in which L represents hydroxy and $R^c$ and $R^d$ each represent hydrogen and the other substituents and indices have the meanings given below.

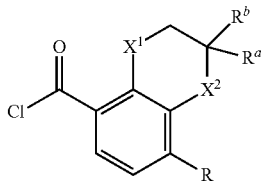

| No. | $X^1$ | $X^2$ | $R^a$ | $R^b$ | R' |
|---|---|---|---|---|---|
| 7-1 | O | S | H | H | $CF_3$ |
| 7-2 | O | S | H | H | $CHF_2$ |
| 7-3 | O | S | H | H | $CF_2CF_3$ |
| 7-4 | O | S(O) | H | H | $CF_3$ |
| 7-5 | O | S(O) | H | H | $CHF_2$ |
| 7-6 | O | S(O) | H | H | $CF_2CF_3$ |
| 7-7 | O | $SO_2$ | H | H | $CF_3$ |
| 7-8 | O | $SO_2$ | H | H | $CHF_2$ |
| 7-9 | O | $SO_2$ | H | H | $CF_2CF_3$ |
| 7-10 | O | S | Me | H | $CF_3$ |
| 7-11 | O | S | Me | H | $CHF_2$ |
| 7-12 | O | S(O) | Me | H | $CF_3$ |
| 7-13 | O | S(O) | Me | H | $CHF_2$ |
| 7-14 | O | $SO_2$ | Me | H | $CF_3$ |
| 7-15 | O | $SO_2$ | Me | H | $CHF_2$ |
| 7-16 | O | S | OMe | H | $CF_3$ |
| 7-17 | O | S | OMe | H | $CHF_2$ |
| 7-18 | O | S(O) | OMe | H | $CF_3$ |
| 7-19 | O | S(O) | OMe | H | $CHF_2$ |
| 7-20 | O | $SO_2$ | OMe | H | $CF_3$ |
| 7-21 | O | $SO_2$ | OMe | H | $CHF_2$ |
| 7-22 | O | S | OEt | H | $CF_3$ |
| 7-23 | O | S | OEt | H | $CHF_2$ |
| 7-24 | O | S(O) | OEt | H | $CF_3$ |
| 7-25 | O | S(O) | OEt | H | $CHF_2$ |
| 7-26 | O | $SO_2$ | OEt | H | $CF_3$ |
| 7-27 | O | $SO_2$ | OEt | H | $CHF_2$ |
| 7-28 | O | S | OH | H | $CF_3$ |
| 7-29 | O | S | OH | H | $CHF_2$ |
| 7-30 | O | S(O) | OH | H | $CF_3$ |
| 7-31 | O | S(O) | OH | H | $CHF_2$ |
| 7-32 | O | $SO_2$ | OH | H | $CF_3$ |
| 7-33 | O | $SO_2$ | OH | H | $CHF_2$ |
| 7-34 | O | S | SMe | H | $CF_3$ |
| 7-35 | O | S | SMe | H | $CHF_2$ |
| 7-36 | O | S(O) | SMe | H | $CF_3$ |
| 7-37 | O | S(O) | SMe | H | $CHF_2$ |
| 7-38 | O | $SO_2$ | SMe | H | $CF_3$ |
| 7-39 | O | $SO_2$ | SMe | H | $CHF_2$ |
| 7-40 | O | S | CN | H | $CF_3$ |
| 7-41 | O | S | CN | H | $CHF_2$ |
| 7-42 | O | S(O) | CN | H | $CF_3$ |
| 7-43 | O | S(O) | CN | H | $CHF_2$ |
| 7-44 | O | $SO_2$ | CN | H | $CF_3$ |
| 7-45 | O | $SO_2$ | CN | H | $CHF_2$ |
| 7-46 | O | S | | C=O | $CF_3$ |
| 7-47 | O | S | | C=O | $CHF_2$ |
| 7-48 | O | S(O) | | C=O | $CF_3$ |
| 7-49 | O | S(O) | | C=O | $CHF_2$ |
| 7-50 | O | $SO_2$ | | C=O | $CF_3$ |
| 7-51 | O | $SO_2$ | | C=O | $CHF_2$ |
| 7-52 | O | S | | C=S | $CF_3$ |
| 7-53 | O | S | | C=S | $CHF_2$ |
| 7-54 | O | S(O) | | C=S | $CF_3$ |
| 7-55 | O | S(O) | | C=S | $CHF_2$ |
| 7-56 | O | $SO_2$ | | C=S | $CF_3$ |
| 7-57 | O | $SO_2$ | | C=S | $CHF_2$ |
| 7-58 | S | O | H | H | $CF_3$ |
| 7-59 | S | O | H | H | $CHF_2$ |
| 7-60 | S(O) | O | H | H | $CF_3$ |
| 7-61 | S(O) | O | H | H | $CHF_2$ |
| 7-62 | $SO_2$ | O | H | H | $CF_3$ |
| 7-63 | $SO_2$ | O | H | H | $CHF_2$ |

Compounds of the formula (I) according to the invention can be prepared, for example, by the methods specified in WO2012/028579 A1. The required compounds of the formula (II') can be prepared, e.g., using the synthetic route described in scheme 1.

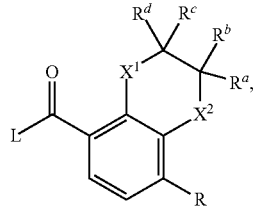

(II')

in which the symbols and indices have the following meanings:

L represents halogen or $R^3O$, $R^3$ represents hydrogen or $(C_1-C_6)$-alkyl, $X^1$, $X^2$ independently of one another each represent O or S(O), R represents halo-$(C_1-C_3)$-alkyl, $R^a$, $R^b$, $R^c$, $R^d$ independently of one another each represent hydrogen, fluorine, chlorine, hydroxy, $(C_1-C_6)$-alkyl, halo-$(C_1-C_6)$-alkyl, $(C_1-C_6)$-alkyloxy, $(C_1-C_6)$-alkylthio, cyano, or $R^a$ and $R^b$ or $R^c$ and $R^d$ together represent an oxo or a thiooxo group, n represents 0, 1 or 2.

The substituents L, R, $R^a$, $R^b$, $R^c$, $R^d$, $X^1$ and $X^2$ have the meanings given for compounds of the formula (II') in the formulae shown in the schemes below. LG represents a leaving group such as, for example, halide or sulfonate. Y represents a hydrolysable group such as halide or acyloxy.

Scheme 1

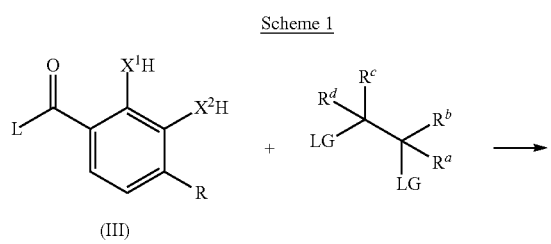

(III)

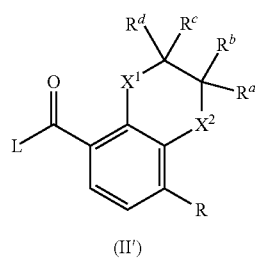

(II')

Scheme 2

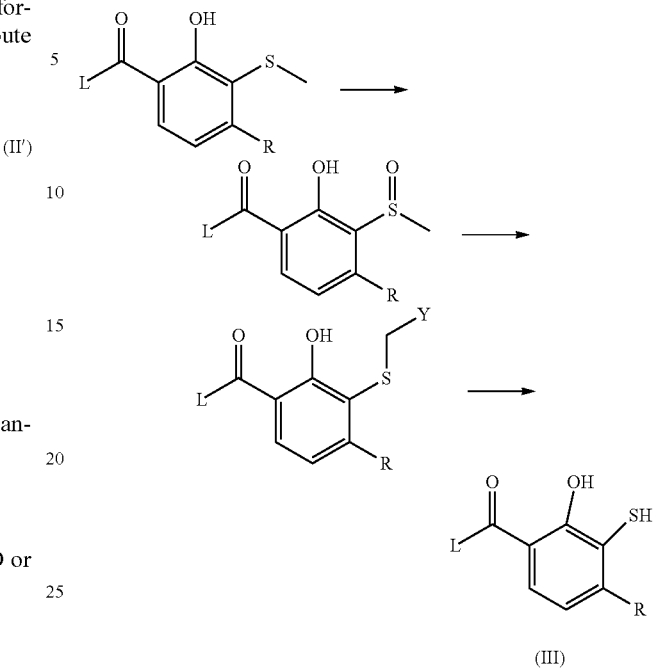

(III)

Compounds of formula (III) in which X represents oxygen and $X^2$ represents sulfur can also be prepared, for example, according to the reaction sequence given in scheme 2—starting from substituted 3-thioalkylsalicylic acid derivatives—by sulfur oxidation, Pummerer rearrangement and hydrolysis. The substituted 3-thioalkylsalicylic acid derivatives are known in principle and/or can be prepared by the methods given in US2015/322003.

Scheme 3

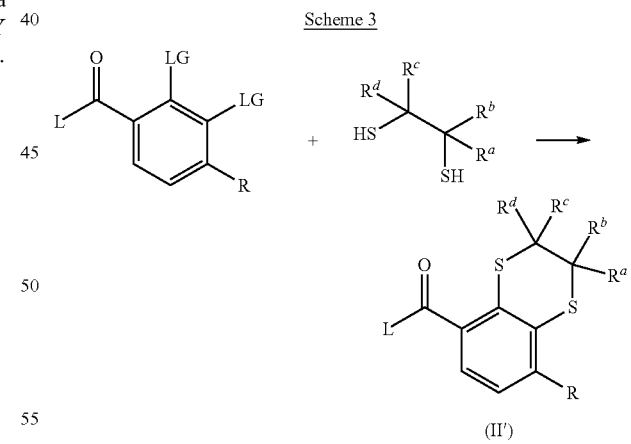

(II')

Compounds of formula (II') in which $X^1$ and $X^2$ represent sulfur can be prepared, for example, according to the reaction sequence given in scheme 3—starting from, for example, substituted 2,3-dihalobenzoic acid derivatives—by means of cyclization via double substitution with an ethane-1,2-dithiol. The 2,3-substituted benzoic acid derivatives are known in principle.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Gunther Jung), Wiley, 1999, on pages 1 to 34.

The compounds of the formula (I) according to the invention (and/or salts thereof), referred to collectively as "compounds according to the invention" hereinafter, have excellent herbicidal efficacy against a broad spectrum of economically important monocotyledonous and dicotyledonous annual harmful plants.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

The compounds according to the invention can be selective in crops of useful plants and can also be employed as non-selective herbicides.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain active compounds used in agroindustry, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further particular properties lie in tolerance or resistance to abiotic stress factors, for example heat, cold, drought, salinity and ultraviolet radiation.

Preference is given to using the compounds of the formula (I) according to the invention or salts thereof in economically important transgenic crops of useful and ornamental plants. The compounds of the formula (I) can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). What has been described are, for example, several cases of genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant), transgenic crop plants, for example cotton, capable of producing *Bacillus thuringiensis* toxins (Bt toxins), which make the plants resistant to particular pests (EP 0142924 A, EP 0193259 A), transgenic crop plants having a modified fatty acid composition (WO 91/013972 A).

genetically modified crop plants having novel constituents or secondary metabolites, for example novel phytoalexins, which cause an increase in disease resistance (EP 0309862 A, EP 0464461 A), genetically modified plants having reduced photorespiration, which have higher yields and higher stress tolerance (EP 0305398 A), transgenic crop plants which produce pharmaceutically or diagnostically important proteins ("molecular pharming"), transgenic crop plants which feature higher yields or better quality, transgenic crop plants which are distinguished by a combination, for example of the abovementioned novel properties ("gene stacking").

Numerous molecular biology techniques which can be used to produce novel transgenic plants with modified properties are known in principle; see, for example, I.

Potrykus and G. Spangenberg (eds), Gene Transfer to Plants, Springer Lab Manual (1995), Springer Verlag Berlin, Heidelberg or Christou, "Trends in Plant Science" 1 (1996) 423-431).

For such genetic manipulations, nucleic acid molecules which allow mutagenesis or sequence alteration by recombination of DNA sequences can be introduced into plasmids. With the aid of standard methods, it is possible, for example, to undertake base exchanges, remove part sequences or add natural or synthetic sequences. To join the DNA fragments with one another, adapters or linkers can be placed onto the fragments, see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants. Thus, transgenic plants can be obtained whose properties are altered by overexpression, suppression or inhibition of homologous (=natural) genes or gene sequences or expression of heterologous (=foreign) genes or gene sequences.

The compounds (I) according to the invention can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds, or to any desired combinations of these active compounds.

The compounds of the invention can be used with particular preference in transgenic crop plants which are resistant to a combination of glyphosates and glufosinates, glyphosates and sulfonylureas or imidazolinones. Most preferably, the compounds according to the invention can be used in transgenic crop plants such as corn or soya with the trade name or the designation Optimum™ GAT™ (glyphosate ALS tolerant), for example.

When the active compounds of the invention are employed in transgenic crops, not only do the effects towards harmful plants observed in other crops occur, but frequently also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds according to the invention of the formula (as herbicides for controlling harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. These individual formulation types are known in principle and are described, for example, in: Winnacker-Küchler, "Chemische Technologie [Chemical Technology]", Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th Ed. 1986.

On the basis of these formulations, it is also possible to produce combinations with other active compounds, for example insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as are described in, for example, Weed Research 26 (1986) 441-445 or "The Pesticide Manual", 16th edition, The British Crop Protection Council and the Royal Soc. of Chemistry, 2006 and the literature cited therein. Known herbicides or plant growth regulators which can be combined with the compounds according to the invention are, for example, the following, where said active compounds are designated either with their "common name" in accordance with the International Organization for Standardization (ISO) or with the chemical name or with the code number. They always encompass all of the application forms such as, for example, acids, salts, esters and also all isomeric forms such as stereoisomers and optical isomers, even if they are not explicitly mentioned.

Examples of such herbicidal mixing partners are:

acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammonium sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, -isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat dibromide, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. 0-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxyniloctanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorophenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrione, sulfentrazone, sulfometuron, sulfometuron-methyl, sulfosulfuron, SYN-523, SYP-249, i.e. 1-ethoxy-3-methyl-1-oxobut-3-en-2-yl5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazine, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy] benzyl}aniline, and also the following compounds:

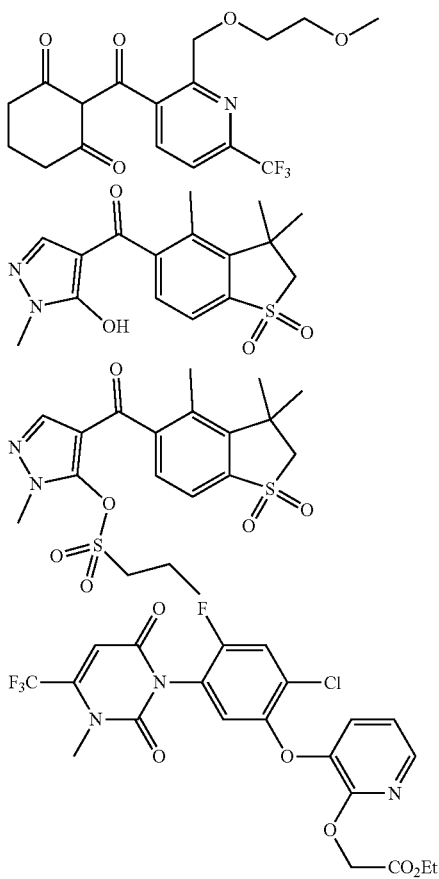

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenoxide mixture, 4-oxo-4 [(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Safeners which can be employed in combination with the compounds of the formula (I) according to the invention and optionally in combination with further active compounds such as insecticides, acaricides, herbicides, fungicides as listed above are preferably selected from the group consisting of:

S1) Compounds of the formula (S1),

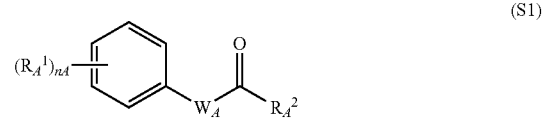

(S1)

where the symbols and indices are defined as follows:
$n_A$ represents a natural number from 0 to 5, preferably from 0 to 3;
$R_A^1$ represents halogen, $(C_1-C_4)$-alkyl, $(C_1-C_4)$-alkoxy, nitro or $(C_1-C_4)$-haloalkyl;
$W_A$ represents an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$,

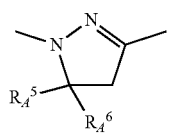
(W$_A^1$)

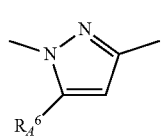
(W$_A^2$)

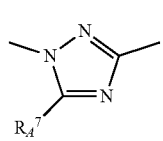
(W$_A^3$)

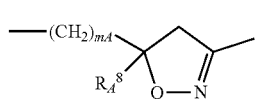
(W$_A^4$)

$m_A$ represents 0 or 1;

$R_A^2$ represents $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;

$R_A^3$ represents hydrogen or an unsubstituted or substituted aliphatic hydrocarbon radical, preferably having a total of 1 to 18 carbon atoms;

$R_A^4$ represents hydrogen, $(C_1-C_6)$-alkyl, $(C_1-C_6)$-alkoxy or substituted or unsubstituted phenyl;

$R_A^5$ represents H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ represents hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and represent hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2),

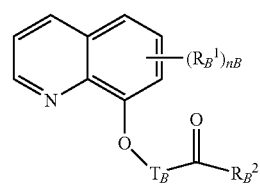

(S2)

where the symbols and indices are defined as follows:

$R_B^1$ represents halogen, $(C_1-C_4)$-alkyl, $(C_1-C_4)$-alkoxy, nitro or $(C_1-C_4)$-haloalkyl;

$n_B$ represents a natural number from 0 to 5, preferably from 0 to 3;

$R_B^2$ represents $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B^3$ represents hydrogen or an unsubstituted or substituted aliphatic hydrocarbon radical, preferably having a total of 1 to 18 carbon atoms;

$R_B^4$ represents hydrogen, $(C_1-C_6)$-alkyl, $(C_1-C_6)$-alkoxy or substituted or unsubstituted phenyl;

$T_B$ represents a ($C_1$ or $C_2$)-alkanediyl chain which is unsubstituted or substituted by one or two $(C_1-C_4)$-alkyl radicals or by [$(C_1-C_3)$-alkoxy]carbonyl;

preferably:

a) compounds of the 8-quinolinoxyacetic acid type (S2a), preferably 1-methylhexyl (5-chloro-8-quinolinoxy)acetate ("cloquintocet-mexyl") (S2-1), (1,3-dimethylbut-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

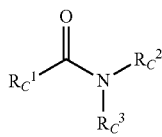

where the symbols and indices are defined as follows:
$R^c$ represents $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and represent hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:
active compounds of the dichloroacetamide type, which are frequently used as pre-emergence safeners (soil-acting safeners), for example
"dichlormid" (N,N-diallyl-2,2-dichloroacetamide) (S3-1),
"R-29148" (3-dichloroacetyl-2,2,5-trimethyl-1,3-oxazolidine) from Stauffer (S3-2),
"R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N-[(allylaminocarbonyl)methyl]dichloroacetamide) from Sagro-Chem (S3-6),
"AD-67" or "MON 4660" (3-dichloroacetyl-1-oxa-3-azaspiro[4.5]decane) from Nitrokemia or Monsanto (S3-7),
"TI-35" (1-dichloroacetylazepane) from TRI-Chemical RT (S3-8),
"diclonon" (dicyclonon) or "BAS145138" or "LAB145138" (S3-9)
((RS)-1-dichloroacetyl-3,3,8a-trimethylperhydropyrrolo[1,2-a]pyrimidin-6-one) from BASF,
"furilazole" or "MON 13900" ((RS)-3-dichloroacetyl-5-(2-furyl)-2,2-dimethyloxazolidine) (S3-10); and the (R) isomer thereof (S3-11).

S4) N-acylsulfonamides of the formula (S4) and salts thereof,

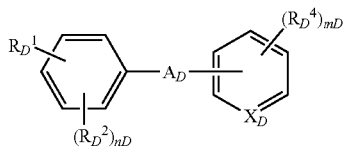

in which the symbols and indices are defined as follows:
$A_D$ represents $SO_2-NR_D^3-CO$ or $CO-NR_D^3-SO_2$
$X_D$ represents CH or N;
$R_D^1$ represents $CO-NR_D^5R_D^6$ or $NHCO-R_D^1$;
$R_D^2$ represents halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ represents hydrogen, $(C_1-C_4)$-alkyl, $(C_2-C_4)$-alkenyl or $(C_2-C_4)$-alkynyl;
$R_D^4$ represents halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;
$R_D^5$ represents hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group consisting of nitrogen, oxygen and sulfur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ represents hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or
$R_D^5$ and $R_D^6$ together with the nitrogen atom carrying them form a pyrrolidinyl or piperidinyl radical;
$R_D^7$ represents hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$n_D$ represents 0, 1 or 2;
$m_D$ represents 1 or 2;
$v_D$ represents 0, 1, 2 or 3;

among these, preference is given to compounds of the N-acylsulfonamide type, for example of the formula (S4a) below, which are known, for example, from WO-A-97/45016

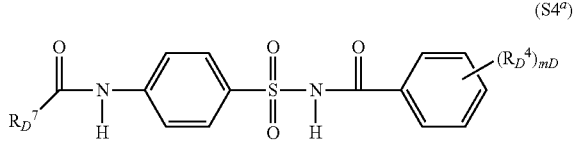

in which
$R_D^7$ represents $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$R_D^4$ represents halogen, $(C_1-C_4)$-alkyl, $(C_1-C_4)$-alkoxy, $CF_3$;
$m_D$ represents 1 or 2;
$v_D$ represents 0, 1, 2 or 3;

and also
acylsulfamoylbenzamides, for example of the formula (S4$^b$) below, which are known, for example, from WO-A-99/16744,

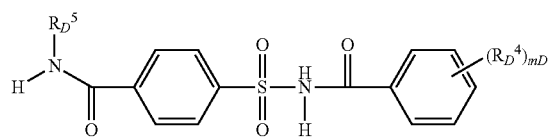

e.g. those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and also
compounds of the N-acylsulfamoylphenylurea type, of the formula (S4$^c$), which are known, for example, from EP-A-365484,

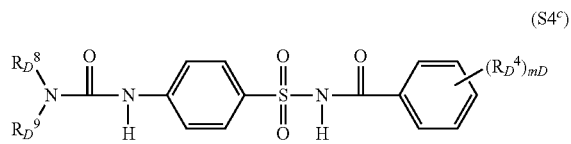

in which
$R_D^8$ and $R_D^9$ independently of one another represent hydrogen, $(C_1\text{-}C_8)$-alkyl, $(C_3\text{-}C_8)$-cycloalkyl, $(C_3\text{-}C_6)$-alkenyl, $(C_3\text{-}C_6)$-alkynyl,
$R_D^4$ represents halogen, $(C_1\text{-}C_4)$-alkyl, $(C_1\text{-}C_4)$-alkoxy, $CF_3$,
$m_D$ represents 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
and also
N-phenylsulfonylterephthalamides of the formula (S4), which are known, for example, from CN 101838227,

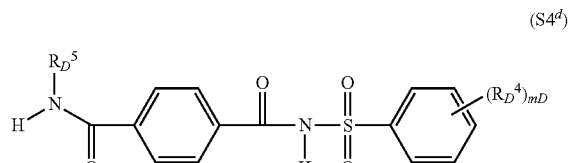

e.g. those in which
$R_D^4$ represents halogen, $(C_1\text{-}C_4)$-alkyl, $(C_1\text{-}C_4)$-alkoxy, $CF_3$;
$m_D$ represents 1 or 2;
$R_D^5$ represents hydrogen, $(C_1\text{-}C_6)$-alkyl, $(C_3\text{-}C_6)$-cycloalkyl, $(C_2\text{-}C_6)$-alkenyl, $(C_2\text{-}C_6)$-alkynyl, $(C_5\text{-}C_6)$-cycloalkenyl.

S5) Active compounds from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

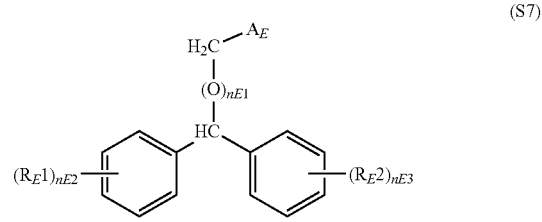

in which the symbols and indices are defined as follows:
$R_E^1$, $R_E^2$ independently of one another represent halogen, $(C_1\text{-}C_4)$-alkyl, $(C_1\text{-}C_4)$-alkoxy, $(C_1\text{-}C_4)$-haloalkyl, $(C_1\text{-}C_4)$-alkylamino, di-$(C_1\text{-}C_4)$-alkylamino, nitro;
$A_E$ represents $COOR_E^3$ or $COSR_E^4$
$R_E^3$, $R_E^4$ independently of one another represent hydrogen, $(C_1\text{-}C_4)$-alkyl, $(C_2\text{-}C_6)$-alkenyl, $(C_2\text{-}C_4)$-alkynyl, cyanoalkyl, $(C_1\text{-}C_4)$-haloalkyl, phenyl, nitrophenyl, benzyl, halobenzyl, pyridinylalkyl and alkylammonium,
$n_E^1$ represents 0 or 1
$n_E^2$, $n_E^3$ independently of one another represent 0, 1 or 2, preferably:
diphenylmethoxyacetic acid,
ethyl diphenylmethoxyacetate,
methyl diphenylmethoxyacetate (CAS reg. no. 41858-19-9) (S7-1).

S8) Compounds of the formula (S8), as described in WO-A-98/27049,

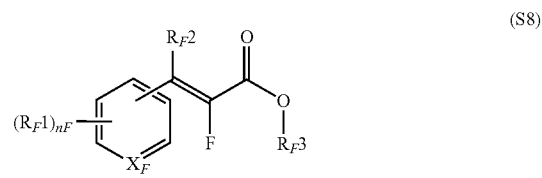

in which
$X_F$ represents CH or N,
$n_F$ in the case that $X_F$=N is an integer from 0 to 4 and in the case that $X_F$=CH is an integer from 0 to 5,
$R_F^1$ represents halogen, $(C_1\text{-}C_4)$-alkyl, $(C_1\text{-}C_4)$-haloalkyl, $(C_1\text{-}C_4)$-alkoxy, $(C_1\text{-}C_4)$-haloalkoxy, nitro, $(C_1\text{-}C_4)$-alkylthio, $(C_1-C_4)$-alkylsulfonyl, $(C_1-C_4)$-alkoxycarbonyl, optionally substituted phenyl, optionally substituted phenoxy, $R_F^2$ represents hydrogen or $(C_1-C_4)$-alkyl, $R_F^3$ represents hydrogen, $(C_1-C_8)$-alkyl, $(C_1-C_4)$-alkenyl, $(C_1-C_4)$-alkynyl or aryl, where each of the abovementioned carbon-containing radicals is unsubstituted or substituted by one or more, preferably up to three identical or different radicals from the group consisting of halogen and alkoxy; or salts thereof, preferably compounds in which $X_F$ represents CH, $n_F$ represents an integer from 0 to 2, $R_F^1$ represents halogen, $(C_1-C_4)$-alkyl, $(C_1-C_4)$-haloalkyl, $(C_1-C_4)$-alkoxy, $(C_1-C_4)$-haloalkoxy, $R_F^2$ represents hydrogen or $(C_1-C_4)$-alkyl, $R_F^3$ represents hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the formulae (S10a) or (S10$^b$) as described in WO-A-2007/023719 and WO-A-2007/023764

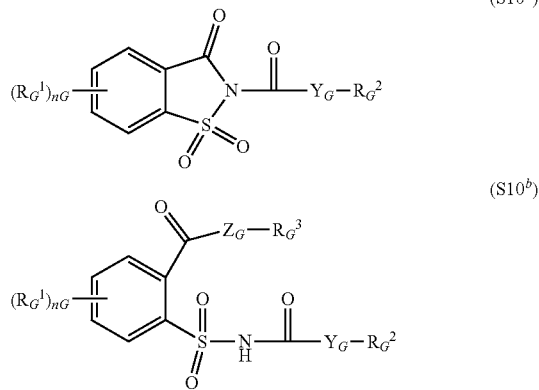

in which $R_G^1$ represents halogen, $(C_1-C_4)$-alkyl, methoxy, nitro, cyano, $CF_3$, $OCF_3$, $Y_G$, $Z_G$ independently of one another represent O or S, $n_G$ represents an integer from 0 to 4, $R_G^2$ represents $(C_1-C_{16})$-alkyl, $(C_2-C_6)$-alkenyl, $(C_3-C_6)$-cycloalkyl, aryl; benzyl, halobenzyl, $R_G^3$ represents hydrogen or $(C_1-C_6)$-alkyl.

S11) Active compounds of the oxyimino compound type (S11), which are known as seed-dressing agents, for example "oxabetrinil" ((Z)-1,3-dioxolan-2-ylmethoxyimino(phenyl)acetonitrile) (S11-1), which is known as a seed-dressing safener for millet/Sorghum against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/Sorghum against metolachlor damage, and "cyometrinil" or "CGA-43089" ((Z)-cyanomethoxyimino(phenyl)acetonitrile) (S11-3), which is known as a seed-dressing safener for millet/Sorghum against metolachlor damage.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):

"naphthalic anhydride" (1,8-naphthalenedicarboxylic anhydride) (13-1), which is known as a seed-dressing safener for corn against thiocarbamate herbicide damage, "fenclorim" (4,6-dichloro-2-phenylpyrimidine) (13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/Sorghum against alachlor and metolachlor damage, "CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS Reg. No. 96420-72-3) (2-dichloromethyl-2-methyl-1,3-dioxolane) (S13-5) from Nitrokemia, which is known as a safener for corn, "MG 838" (CAS Reg. No. 133993-74-5)

(2-propenyl 1-oxa-4-azaspiro[4.5]decane-4-carbodithioate) (S13-6) from Nitrokemia, "disulfoton" (0,0-diethyl S-2-ethylthioethylphosphorodithioate) (S13-7), "dietholate" (0,0-diethyl 0-phenyl phosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY 93" (S-1-methyl 1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against imazosulfuron herbicide damage, "cumyluron"="JC 940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

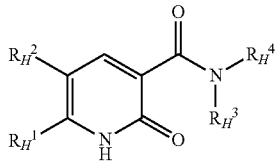

(S15)

as described in WO-A-2008/131861 and WO-A-2008/131860 in which $R_H^1$ represents a $(C_1-C_6)$-haloalkyl radical and
$R_H^2$ represents hydrogen or halogen and
$R_H^3$, $R_H^4$ independently of one another represent hydrogen, $(C_1-C_6)$-alkyl, $(C_2-C_{16})$-alkenyl or $(C_2-C_{16})$-alkynyl,
where each of the 3 last-mentioned radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3—C)$-cycloalkyl which is unsubstituted or substituted, phenyl which is unsubstituted or substituted, and heterocyclyl which is unsubstituted or substituted,
or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring,
where each of the 4 last-mentioned radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted,
or
$R_H^3$ represents $(C_1-C_4)$-alkoxy, $(C_2-C_4)$-alkenyloxy, $(C_2-C_6)$-alkynyloxy or $(C_2-C_4)$-haloalkoxy and
$R_H^4$ represents hydrogen or $(C_1-C_4)$-alkyl or
$R_H^3$ and $R_H^4$ together with the directly attached nitrogen atom represent a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Particularly preferred safeners are mefenpyr-diethyl, cyprosulfamide, isoxadifen-ethyl, cloquintocet-mexyl and dichlormid.

Wettable powders are preparations uniformly dispersible in water which, in addition to the active compound and apart from a diluent or inert substance, also comprise surfactants of ionic and/or nonionic type (wetting agent, dispersant), e.g. polyethoxylated alkylphenols, polyethoxylated fatty alcohols, polyethoxylated fatty amines, fatty alcohol poly glycolethersulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan esters, for example sorbitan fatty acid esters, or polyoxyethylene sorbitan esters, for example polyoxyethylene sorbitan fatty esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention. In wettable powders, the active compound concentration is, for example, about 10 to 90% by weight, the remainder to 100% by weight consisting of customary formulation constituents. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

A carrier is a natural or synthetic, organic or inorganic substance with which the active compounds are mixed or combined for better applicability, in particular for application to plants or plant parts or seed. The carrier, which may be solid or liquid, is generally inert and should be suitable for use in agriculture. Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. It is likewise possible to use mixtures of such carriers. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks Suitable liquefied gaseous extenders or carriers are liquids which are gaseous at standard temperature and under atmospheric pressure, for example aerosol propellants such as halogenated hydrocarbons, or else butane, propane, nitrogen and carbon dioxide.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

When the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The compositions according to the invention may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is necessary if one of the active compounds and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active compounds can be combined with any solid or liquid additive commonly used for formulation purposes. In general, the compositions and formulations according to the invention contain between 0.05 and 99% by weight, 0.01 and 98% by weight, preferably between 0.1 and 95% by weight and more preferably between 0.5 and 90% active compound, most preferably between 10 and 70 percent by weight. The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be produced in a manner known per se, for example by mixing the active compounds with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The compositions according to the invention include not only formulations which are already ready for use and can be deployed with a suitable apparatus onto the plant or the seed, but also commercial concentrates which have to be diluted with water prior to use.

The active compounds according to the invention may be present as such or in their (commercial standard) formulations, or else in the use forms prepared from these formulations as a mixture with other (known) active compounds, such as insecticides, attractants, sterilants, bactericides, acaricides, nematicides, fungicides, growth regulators, herbicides, fertilizers, safeners or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

As also described below, the treatment of transgenic seed with the active compounds according to the invention or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight.

Alternatively, it is also possible to use seed which, after drying, for example, has been treated with water and then dried again.

In general, when treating the seed, it has to be ensured that the amount of the composition according to the invention and/or further additives applied to the seed is chosen such that the germination of the seed is not impaired and the plant which arises therefrom is not damaged. This has to be ensured particularly in the case of active compounds which can exhibit phytotoxic effects at certain application rates.

The compositions according to the invention can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272,417 A, 4,245,432 A, 4,808,430, 5,876,739, US 2003/0176428 A1, WO 2002/080675 A1, WO 2002/028186 A2.

The active compounds according to the invention can be converted to the customary seed-dressing formulations, such as solutions, emulsions, suspensions, powders, foams, slurries or other coating compositions for seed, and also ULV formulations.

These formulations are produced in a known manner, by mixing the active compounds with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulfated derivatives thereof.

Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances usable for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

The seed-dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For the treatment of seed with the seed-dressing formulations usable in accordance with the invention or with the preparations prepared therefrom by addition of water, useful equipment is all mixing units usable customarily for seed dressing. Specifically, the seed dressing procedure is to place the seed into a mixer, to add the particular desired amount of seed-dressing formulations, either as such or after prior dilution with water, and to mix them until the formulation is distributed homogeneously on the seed. If appropriate, this is followed by a drying operation.

The active compounds according to the invention, given good plant compatibility, favorable homeotherm toxicity and good environmental compatibility, are suitable for protection of plants and plant organs, for increasing harvest yields, and for improving the quality of the harvested crop. They can preferably be used as crop protection agents. They are active against normally sensitive and resistant species and also against all or specific stages of development.

Plants which can be treated in accordance with the invention include the following main crop plants: corn, soya bean, cotton, *Brassica* oil seeds such as *Brassica napus* (e.g. Canola), *Brassica rapa*, *B. juncea* (e.g. (field) mustard) and *Brassica carinata*, rice, wheat, sugar beet, sugar cane, oats, rye, barley, millet and *Sorghum*, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, eggplants), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and chinese cabbage), Leguminosae sp. (for example peanuts, peas, and beans—for example runner beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes and genotypes.

The treatment method according to the invention can be used for the treatment of genetically modified organisms (GMOs), e.g. plants (such as crop plants and trees) or seeds. Genetically modified plants (or transgenic plants) are plants where a heterologous gene has been stably integrated into the genome. The expression "heterologous gene" means essentially a gene which is provided or assembled outside the plant or plant cell and, when it is introduced into the nuclear, chloroplastic or mitochondrial genome, gives the transformed plant new or improved agronomic or other properties, specifically by expressing a protein or polypeptide of interest or by downregulating or silencing one or more other genes present in the plant (using, for example, antisense technology, cosuppression technology, RNA interference (RNAi) technology or microRNA (miRNA) technology). A heterologous gene that has been integrated into the genome is also called a transgene. A transgene which has been integrated into the plant genome is referred to as a transformation event or transgenic event.

Depending on the plant species or plant cultivars, their location and growth conditions (soils, climate, vegetation period, diet), the inventive treatment may also result in superadditive ("synergistic") effects. For example, the following effects which exceed the effects actually to be expected are possible: reduced application rates and/or widened spectrum of activity and/or increased efficacy of the active ingredients and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf color, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect on plants. Accordingly, they are suitable for mobilizing the defense system of the plant against attack by unwanted microorganisms. This may possibly be one of the reasons for the enhanced activity of the combinations according to the invention, for example against fungi. Plant-fortifying (resistance-inducing) substances shall be understood to mean, in the present context, also those substances or combinations of substances which are capable of stimulating the defense system of plants in such a way that, when subsequently inoculated with unwanted microorganisms, the plants treated display a substantial degree of resistance to these microorganisms. In the present case, unwanted microorganisms are understood to mean phytopathogenic fungi, bacteria and viruses. The inventive substances can therefore be used for protection of plants from attack by the pathogens mentioned above within a certain period of time after treatment. The period within which protection is achieved generally extends for from 1 to 10 days, preferably 1 to 7 days, after the treatment of the plants with the active ingredients.

Plants and plant cultivars which are preferably treated in accordance with the invention include all plants which have genetic material which imparts particularly advantageous, useful traits to these plants (whether obtained by breeding and/or biotechnological means).

Plants and plant varieties which are likewise preferably treated in accordance with the invention are resistant to one or more biotic stress factors, i.e. said plants have a better defence against animal and microbial pests, such as against nematodes, insects, mites, phytopathogenic fungi, bacteria, viruses and/or viroids.

Examples of nematode- or insect-resistant plants are described, for example, in U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396, 12/497,221, 12/644,632, 12/646,004, 12/701,058, 12/718,059, 12/721,595, 12/638,591 and in WO 11/002992, WO 11/014749, WO 11/103247, WO 11/103248, WO 12/135436, WO 12/135501, WO 2013134523, WO 2013134535, WO 2014036238, WO 2014126986A1 WO 2014138339, WO 2014003769, WO 2015021367, WO 2015021354, WO 2015077525, WO 2015038262, WO 2015041769, WO 2015088937A.

Examples of plant resistances to other types of pathogens are described, for example, in WO 13/050410, WO 2013127988, WO 2013135726, WO 2015036378, WO 2015036469, WO 2015177206.

Plants and plant cultivars which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or lack of shade.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and nonstress conditions), including, but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and resistance to lodging. Further yield traits include seed composition, such as carbohydrate content, protein content, oil content and oil composition, nutritional value, reduction in antinutritional compounds, improved processability and better storage stability.

Plants that may be treated according to the invention are hybrid plants that already express the characteristics of heterosis, or hybrid effect, which results in generally higher yield, vigor, better health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in the case of corn) be produced by flag removal, i.e. mechanical removal of the male sexual organs (or the male flowers); however, it is more common for male sterility to be based on genetic determinants in the plant genome; in particular, if the desired seed material to be harvested from the hybrid plants is the seed, it is usually ensured that male fertility is restored in hybrid plants. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/02069). Other plants which contain male sterility genes and fertility-restoring genes, and systems for hybrid seed production are described, for example, in WO 2014170387 and WO 2014195152.

Plants or plant cultivars (obtained by plant biotechnology methods such as genetic engineering) which may be treated according to the invention also include herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be rendered glyphosate-tolerant in a number of ways. Thus, for example, glyphosate-tolerant plants can be obtained by transforming the plant with a gene encoding the enzyme 5-enolpyruvyl-shikimate-3-phosphate synthase (EPSPS). Examples of such EPSPS genes are the AroA gene (mutant CT7) of the bacterium *Salmonella typhimurium* (Science 1983, 221, 370-371), the CP4 gene of the bacterium *Agrobacterium* sp. (Curr. Topics Plant Physiol. 1992, 7, 139-145), the genes encoding a *petunia* EPSPS (Science 1986, 233, 478-481), a tomato EPSPS (J. Biol. Chem. 1988, 263, 4280-4289) or an *Eleusine* EPSPS (WO 01/66704). It can also be a mutated EPSPS, as described, for example, in EP 0837944, WO 00/66746, WO 00/66747 or WO 02/26995, WO 2011/000498. Glyphosate-tolerant plants can also be obtained by expressing a gene that encodes a glyphosate oxidoreductase enzyme as described in U.S. Pat. Nos. 5,776,760 and 5,463,175. Glyphosate-tolerant plants can also be obtained by expressing a gene that encodes a glyphosate acetyl transferase enzyme as described, for example, in WO 02/036782, WO 03/092360, WO 05/012515 and WO 07/024782. Glyphosate-tolerant plants can also be obtained by selecting plants containing naturally occurring mutations of the abovementioned genes, as described, for example, in WO 01/024615 or WO 03/013226. Plants that express EPSPS genes that impart glyphosate tolerance are described, for example, in U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants that contain other genes that impart glyphosate tolerance, such as decarboxylase genes, are described, for example, in U.S. patent application Ser. Nos. 11/588,811, 11/185,342, 12/364,724, 11/185,560 or 12/423,926.

Other herbicide-resistant plants are, for example, plants made tolerant to herbicides inhibiting the enzyme glutamine synthase, such as bialaphos, phosphinothricin or glufosinate. Such plants can be obtained by expressing an enzyme detoxifying the herbicide, or by using a mutant of the glutamine synthase enzyme that is resistant to inhibition, described, for example, in the U.S. patent application Ser. No. 11/760,602. One example of such an effective detoxifying enzyme is an enzyme encoding a phosphinothricin acetyltransferase (such as the bar or pat protein from *Streptomyces* species). Plants expressing an exogenous phosphinothricin acetyltransferase are described, for example, in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that have been made tolerant to the herbicides inhibiting the enzyme hydroxyphenylpyruvate dioxygenase (HPPD). HPPD is an enzyme that catalyzes the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, according to WO 96/38567, WO 99/24585, WO 99/24586, WO 09/144079, WO 02/046387 or U.S. Pat. No. 6,768,044, WO 11/076877, WO 11/076882, WO 11/076885, WO 11/076889, WO 11/076892, WO 13/026740, WO 13/092552, WO 13/092551, WO 12/092555, WO 2014043435, WO 2015138394, WO 2015135881.

Tolerance to HPPD inhibitors can also be obtained by transforming plants with genes encoding enzymes enabling the formation of homogentisate despite inhibition of the native HPPD enzyme by the HPPD inhibitor. Such plants and genes are described in WO 99/34008 and WO 02/36787. Tolerance of plants to HPPD inhibitors can also be improved by transforming plants with a gene encoding an enzyme having prephenate dehydrogenase activity (PDH activity) in addition to a gene encoding an HPPD-tolerant enzyme, as described in WO 04/024928. In addition, plants can be made more tolerant of HPPD inhibitor herbicides by adding a gene to their genome that encodes an enzyme that is used to metabolize or degrade HPPD inhibitors, such as the CYP450 enzymes shown in WO 07/103567 and WO 08/150473.

Still other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyloxy (thio)benzoates, and/or sulfonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright (Weed Science 2002, 50, 700-712), and also in U.S. Pat. Nos. 5,378,824, 5,378,824, 5,141,870 and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and also in WO 96/33270. Further imidazolinone-tolerant plants are also described, for example, in WO 04/040012, WO 04/106529, WO 05/020673, WO 05/093093, WO 06/007373, WO 06/015376, WO 06/024351 and WO 06/060634. Further sulfonylurea- and imidazolinone-tolerant plants are also described, for example, in WO 07/024782, WO 11/076345, WO 12/058223, WO 12/150335, WO 2013127766, WO 2014090760, WO 2015004242, WO 2015024957, WO 2015082413 and in the U.S. patent application 61/288,958.

Further plants tolerant to imidazolinone and/or sulfonylurea can be obtained by induced mutagenesis, by selection in cell cultures in the presence of the herbicide or by mutation breeding, as described, for example, for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599 or for sunflower in WO 01/065922.

Plants that are tolerant to 2,4-D or dicamba are described, for example, in U.S. Pat. No. 6,153,401.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding the following:

1) an insecticidal crystal protein from *Bacillus thuringiensis* or an insecticidal portion thereof, such as the insecticidal crystal proteins compiled by Crickmore et al. (*Microbiology and Molecular Biology Reviews* 1998, 62, 807-813), updated by Crickmore et al. (2005) in the *Bacillus thuringiensis* toxin nomenclature, online at:
http://www.lifesci.sussex.ac.uk/Home/Neil_Crickmore/Bt/), or insecticidal portions thereof, for example proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 07/107302), or those proteins encoded by synthetic genes as described in WO 2013134523, WO 2013134535 and U.S. patent application Ser. No. 12/249,016, for example; or 2) a crystal protein from *Bacillus thuringiensis* or a portion thereof which is insecticidal in the presence of a second crystal protein other than *Bacillus thuringiensis* or a portion thereof, such as the binary toxin made up of the Cry34 and Cry35 crystal proteins (*Nat. Biotechnol.* 2001, 19, 668-72; *Applied Environm. Microbiol.* 2006, 71, 1765-1774) or the binary toxin made up of the Cry1A or Cry1F protein and the Cry2Aa or Cry2Ab or Cry2Ae protein (U.S. patent application Ser. No. 12/214,022 and EP-A 2 300 618); or 3) a hybrid insecticidal protein comprising parts of different insecticidal crystal proteins from *Bacillus thuringiensis*, such as a hybrid of the proteins of 1) above or a hybrid of the proteins of 2) above, for example the Cry1A.105 protein produced by corn event MON89034 (WO 07/027777); or 4) a protein of any one of points 1) to 3) above where some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT 102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. patent applications 61/126,083 and 61/195,019), or the binary toxin made up of the VIP3 protein and the Cry2Aa or Cry2Ab or Cry2Ae proteins (U.S. patent application Ser. No. 12/214,022 and EP-A 2 300 618); or 10) a protein according to 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

Of course, the insect-resistant transgenic plants, as used herein, also include any plant comprising a combination of genes encoding the proteins of any one of the above classes 1 to 10. In one embodiment, an insect-resistant plant contains more than one transgene encoding a protein of any one of the above classes 1 to 10, to expand the range of the target insect species affected, when using different proteins targeting different target insect species, or to delay insect resistance development to the plants, when using different proteins insecticidal to the same target insect species but having a different mode of action, such as binding to different receptor binding sites in the insect.

In the present context, an "insect-resistant transgenic plant" also includes any plant which contains at least one transgene which comprises a sequence which, when expressed, produces a double-stranded RNA which, when ingested by a plant pest insect, inhibits the growth of this pest insect, as described, for example, in WO 07/080126, WO 06/129204, WO 07/074405, WO 07/080127 and WO 07/035650.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

1) plants which contain a transgene capable of reducing the expression and/or the activity of the poly(ADP-ribose)polymerase (PARP) gene in the plant cells or plants, as described in WO 00/04173, WO 06/045633, EP-A 1 807 519 or EP-A 2 018 431.

2) plants which contain a stress tolerance-enhancing transgene capable of reducing the expression and/or the activity of the PARG encoding genes of the plants or plant cells, as described, for example, in WO 04/090140.

3) plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP-A 1 794 306, WO 06/133827, WO 07/107326, EP-A 1999 263 or WO 07/107326.

Plants or plant cultivars (obtained by plant biotechnology methods such as genetic engineering) which may also be treated according to the invention show altered quantity, quality and/or storage stability of the harvested product and/or altered properties of specific components of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behavior, the gelling strength, the starch granule size and/or the starch granule morphology, is changed in comparison with the synthesized starch in wild-type plant cells or plants, so that this modified starch is better suited to specific applications. These transgenic plants synthesizing a modified starch are disclosed, for example, in EP-A 0 571427, WO 95/04826, EP-A 0 719 338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 04/056999, WO 05/030942, WO 05/030941, WO 05/095632, WO 05/095617, WO 05/095619, WO 2005/095618, WO 05/123927, WO 06/018319, WO 06/103107, WO 06/108702, WO 07/009823, WO 00/22140, WO 06/063862, WO 06/072603, WO 02/034923, WO 08/017518, WO 08/080630, WO 08/080631, WO 08/090008, WO 01/14569, WO 02/79410, WO 03/33540, WO 04/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 05/002359, U.S. Pat. Nos. 5,824,790, 6,013,861, WO 94/04693, WO 94/09144, WO 94/11520, WO 95/35026, WO 97/20936, WO 10/012796, WO 10/003701, WO13/053729, WO13/053730.

2) Transgenic plants which synthesize non-starch carbohydrate polymers or which synthesize non-starch carbohydrate polymers with altered properties in comparison to wild-type plants without genetic modification (for example WO 2015044209). Examples are plants producing polyfructose, especially of the inulin and levan type, as described in EP-A 0 663 956, WO 96/01904, WO 96/21023, WO 98/39460 and WO 99/24593, plants producing alpha-1,4-glucans, as described in WO 95/31553, US 2002031826, U.S. Pat. Nos. 6,284,479, 5,712,107, WO 97/47806, WO 97/47807, WO 97/47808 and WO 00/14249, plants producing alpha-1,6-branched alpha-1,4-glucans, as described in WO 00/73422, and plants producing alternan, as described in WO 00/47727, WO 00/73422, U.S. Pat. No. 5,908,975 and EP-A 0 728 213.

3) Transgenic plants which produce hyaluronan, as described, for example, in WO 06/032538, WO 07/039314, WO 07/039315, WO 07/039316, JP-A 2006-304779 and WO 05/012529.

4) Transgenic plants or hybrid plants such as bulbs with features such as 'high soluble solids content', 'mild' (low pungency, LP) and/or 'long storage' (LS), as described in U.S. patent application Ser. No. 12/020,360.

5) Transgenic plants which indicate an increasing yield, as disclosed, for example, in WO 11/095528, WO 2014161908, WO 2015032428 or WO 2015117265.

6) Plants, including transgenic plants, which provide fruits or vegetables with improved properties, as described in WO 2013156204, WO 2013120781, WO 2014090968, WO 2014049002, WO 2014079896, WO 2014118150, WO 2015040098A1.

Plants or plant cultivars (which can be obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 98/00549;

b) plants, such as cotton plants, which contain an altered form of rsw2 or rsw3 homologous nucleic acids, as described in WO 04/053219;

c) plants, such as cotton plants, with an increased expression of sucrose phosphate synthase, as described in WO 01/17333;

d) plants, such as cotton plants, with an increased expression of sucrose synthase as described in WO 02/45485;

e) plants, such as cotton plants, wherein the timing of the plasmodesmatal gating at the basis of the fiber cell is altered, for example through downregulation of fiber-selective $-1,3-glucanase as described in WO 05/017157 or WO 09/143995;

f) plants, such as cotton plants, which have fibers with altered reactivity, for example through the expression of the N-acetylglucosaminetransferase gene including nodC and chitin synthase genes, as described in WO 06/136351, WO 2011/089021, WO 2011/089021, WO 2012/074868 and WO 2015140191.

Plants or plant cultivars (which can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content, as described, for example, in U.S. Pat. Nos. 5,969,169, 5,840,946, 6,323,392, 6,063,947 or WO 2014006158, WO 2014006159, WO 2014006162;

b) plants, such as oilseed rape plants, which produce oil having a low linolenic acid content, as described in U.S. Pat. Nos. 6,270,828, 6,169,190 or 5,965,755, WO 2011/060946;

c) plants, such as oilseed rape plants, which produce oil having a low content of saturated fatty acids, as described, for example, in U.S. Pat. No. 5,434,283 or U.S. patent application Ser. No. 12/668,303 or WO 2014006158, WO 2014006159.

Plants or plant cultivars (which can be obtained by plant biotechnology methods such as genetic engineering) which may also be treated according to the invention are plants, such as oilseed rape or related *Brassica* plants, with altered seed scattering properties. Such plants can be obtained by genetic transformation or by selection of plants containing a mutation which confer such modified seed scattering properties; these include oilseed rape plants having delayed or reduced seed scattering as described in U.S. patent application 61/135,230, WO 09/068313 and WO 10/006732.

Plants or plant cultivars (which can be obtained by plant biotechnology methods such as genetic engineering) which may also be treated according to the invention are plants, such as tobacco plants, with altered posttranslational protein modification patterns as described, for example, in WO 10/121818 and WO 10/145846.

Transgenic useful plants which can be treated according to the invention are preferably plants which comprise transformation events or a combination of transformation events and which are listed, for example, in the databases of various national or regional registration agencies, including Event 531/PV-GHBK04 (cotton, insect control, described in WO 2002/040677); Event 1143-14A (cotton, insect control, not deposited, described in WO 06/128569); Event 1143-51B (cotton, insect control, not deposited, described in WO 06/128570); Event 1445 (cotton, herbicide tolerance, not deposited, described in US-A 2002-120964 or WO 02/034946); Event 17053 (rice, herbicide tolerance, deposited as PTA-9843, described in WO 10/117737); Event 17314 (rice, herbicide tolerance, deposited as PTA-9844, described in WO 10/117735); Event 281-24-236 (cotton, insect control—herbicide tolerance, deposited as PTA-6233, described in WO 05/103266 or US-A 2005-216969); Event 3006-210-23 (cotton, insect control—herbicide tolerance, deposited as PTA-6233, described in US-A 2007-143876 or WO 05/103266); Event 3272 (corn, quality trait, deposited as PTA-9972, described in WO 06098952 or US-A 2006-230473); Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO 11/075595); Event 5307 (corn, insect control, deposited as ATCC PTA-9561, described in WO 10/077816); Event ASR-368 (bent grass, herbicide tolerance, deposited as ATCC PTA-4816, described in US-A 2006-162007 or WO 04/053062); Event B16 (corn, herbicide tolerance, not deposited, described in US-A 2003-126634); Event BPS-CV127-9 (soybean, herbicide tolerance, deposited as NCIMB No. 41603, described in WO 10/080829); Event BLR1 (oilseed rape plants, recultivation of male sterility, deposited as NCIMB 41193, described in WO 2005/074671), Event CE43-67B (cotton, insect control, deposited as DSM ACC2724, described in US-A 2009-217423 or WO 06/128573); Event CE44-69D (cotton, insect control, not deposited, described in US-A 2010-0024077); Event CE44-69D (cotton, insect control, not deposited, described in WO 06/128571); Event CE46-02A (cotton, insect control, not deposited, described in WO 06/128572); Event COT102 (cotton, insect control, not deposited, described in US-A 2006-130175 or WO 04/039986); Event COT202 (cotton, insect control, not deposited, described in US-A 2007-067868 or WO 05/054479); Event COT203 (cotton, insect control, not deposited, described in WO 05/054480); Event DAS21606-3/1606 (soybean, herbicide tolerance, deposited as PTA-11028, described in WO 012/033794), Event DAS40278 (corn, herbicide tolerance, deposited as ATCC PTA-10244, described in WO 11/022469); Event DAS-44406-6/pDAB8264.44.06.1 (soybean, herbicide tolerance, deposited as PTA-11336, described in WO 2012/075426), Event DAS-14536-7/pDAB8291.45.36.2 (soybean, herbicide tolerance, deposited as PTA-11335, described in WO 2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO 09/100188); Event DAS68416 (soybean, herbicide tolerance, deposited as ATCC PTA-10442, described in WO 11/066384 or WO 11/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO 08/054747); Event DP-32138-1 (corn, hybrid system, deposited as ATCC PTA-9158, described in US-A 2009-0210970 or WO 09/103049); Event DP-356043-5 (soybean, herbicide tolerance, deposited as ATCC PTA-8287, described in US-A 2010-0184079 or WO 08/002872); Event EE-1 (aubergine, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO 2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO 08/151780); Event GHB614 (cotton, herbicide tolerance, deposited as ATCC PTA-6878, described in US-A 2010-050282 or WO 07/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 10/076212); Event H7-1 (sugar beet, herbicide tolerance, deposited as NCIMB 41158 or NCIMB 41159, described in US-A 2004-172669 or WO 04/074492); Event JOPLIN1 (wheat, fungus resistance, not deposited, described in US-A 2008-064032); Event LL27 (soybean, herbicide tolerance, deposited as NCIMB41658, described in WO 06/108674 or US-A 2008-320616); Event LL55 (soybean, herbicide tolerance, deposited as NCIMB 41660, described in WO 06/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468, 747 or WO 00/026345); Event LLRice62 (rice, herbicide tolerance, deposited as ATCC-203352, described in WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 05/061720); Event MIR162 (corn, insect control, deposited as PTA-8166, described in US-A 2009-300784 or WO 07/142840); Event MIR604 (corn, insect control, not deposited, described in US-A 2008-167456 or WO 05/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 04/011601 or US-A 2006-095986); Event MON87427 (corn, pollination control, deposited as ATCC PTA-7899, described in WO 11/062904); Event MON87460 (corn, stress tolerance, deposited as ATCC PTA-8910, described in WO 09/111263 or US-A 2011-0138504); Event MON87701 (soybean, insect control, deposited as ATCC PTA-8194, described in US-A 2009-130071 or WO 09/064652); Event MON87705 (soybean, quality trait—herbicide tolerance, deposited as ATCC PTA-9241, described in US-A 2010-0080887 or WO 10/037016); Event MON87708 (soybean, herbicide tolerance, deposited as ATCC PTA-9670, described in WO 11/034704); Event MON87712 (soybean, yield, deposited as ATCC PTA-10296, described in WO 12/051199); Event MON87754 (soybean, quality trait, deposited as ATCC PTA-9385, described in WO 10/024976); Event MON87769 (soybean, quality trait, deposited as ATCC PTA-8911, described in US-A 2011-0067141 or WO 09/102873); Event MON88017 (corn, insect control—herbicide tolerance, deposited as ATCC PTA-5582, described in US-A 2008-028482 or WO 05/059103); Event MON88913 (cotton, herbicide tolerance, deposited as ATCC PTA-4854, described in WO 04/072235 or US-A 2006-059590); Event MON88302 (oilseed rape plant, herbicide tolerance, deposited as PTA-10955, described in WO 2011/153186); Event MON88701 (cotton, herbicide tolerance, deposited as PTA-11754, described in WO 2012/134808); Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO 06/130436); Event MS11 (oilseed rape, pollination control—herbicide tolerance, deposited as ATCC PTA-850 or PTA-2485, described in WO 1/031042); Event MS8 (oilseed rape, pollination control—herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 08/114282); Event RF3 (oilseed rape, pollination control—herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event SYHTOH2/SYN-00H2-5 (soybean, herbicide tolerance, deposited as PTA-11226, described in WO 2012/082548); Event T227-1 (sugar beet, herbicide tolerance, not deposited, described in WO 02/44407 or US-A 2009-265817); Event T25 (corn, herbicide tolerance, not deposited, described in US-A 2001-29014 or WO 01/051654); Event T304-40 (cotton, insect control—herbicide tolerance, deposited as ATCC PTA-8171, described in US-A 2010-077501 or WO 08/122406); Event T342-142 (cotton, insect control, not deposited, described in WO 06/128568); Event TC1507 (corn, insect control—herbicide tolerance, not deposited, described in US-A 2005-039226 or WO 04/099447); Event VIP1034 (corn, insect control—herbicide tolerance, deposited as ATCC PTA-3925, described in WO 03/052073); Event 32316 (corn, insect control—herbicide tolerance, deposited as PTA-11507, described in WO 11/084632); Event 4114 (corn, insect control—herbicide tolerance, deposited as PTA-11506, described in WO 11/084621); Event EE-GM3/FG72 (soybean, herbicide tolerance, ATCC accession number PTA-11041, WO 2011/063413A2); Event DAS-68416-4 (soybean, herbicide tolerance, ATCC accession number PTA-10442, WO2011/066360A1); Event DAS-68416-4 (soybean, herbicide tolerance, ATCC accession number PTA-10442, WO 2011/066384A1); Event DP-040416-8 (corn, insect control, ATCC accession number PTA-11508, WO 2011/075593A1); Event DP-043A47-3 (corn, insect control, ATCC accession number PTA-11509, WO 2011/075595A1), Event DP-004114-3 (corn, insect control, ATCC accession number PTA-11506, WO 2011/084621A1); Event DP-032316-8 (corn, insect control, ATCC accession number PTA-11507, WO 2011/084632A1); Event MON-88302-9 (oilseed rape plant, herbicide tolerance, ATCC accession number PTA-10955, WO 2011/153186A1); Event DAS-21606-3 (soybean, herbicide tolerance, ATCC accession number PTA-11028, WO 2012/033794A2); Event MON-87712-4 (soybean plant, quality trait, ATCC accession number PTA-10296, WO 2012/051199A2); Event DAS-44406-6 (soybean, stacked herbicide tolerance, ATCC accession number PTA-11336, WO 2012/075426A1); Event DAS-14536-7 (soybean, stacked herbicide tolerance, ATCC accession number PTA-11335, WO 2012/075429A1); Event SYN-000H2-5 (soybean, stacked herbicide tolerance, ATCC accession number PTA-11226, WO 2012/082548A2); Event DP-061061-7 (oilseed rape plant, herbicide tolerance, not deposited, WO 2012071039A1); Event DP-073496-4 (oilseed rape plant, herbicide tolerance, not deposited, US2012131692); Event 8264.44.06.1 (soybean, stacked herbicide tolerance, ATCC accession number PTA-11336, WO 2012075426A2); Event 8291.45.36.2 (soybean, stacked herbicide tolerance, ATCC accession number PTA-11335, WO 2012075429A2); Event SYHTOH2 (soybean, ATCC accession number PTA-11226, WO 2012/082548A2); Event MON88701 (cotton, ATCC accession number PTA-11754, WO 2012/134808A1); Event KK179-2 (alfalfa, ATCC accession number PTA-11833, WO2013003558A1); Event pDAB8264.42.32.1 (soybean, stacked herbicide tolerance, ATCC accession number PTA-11993, WO 2013010094A1); Event MZDT09Y (corn, ATCC accession number PTA-13025, WO 2013012775A1); Event KK179-2 (alfalfa, ATCC accession number PTA-11833, WO2013003558A1); Event pDAB8264.42.32.1 (soybean, stacked herbicide tolerance, ATCC accession number PTA-11993, WO2013010094A1); Event MZDT09Y (corn, ATCC accession number PTA-13025, WO2013012775A1); Event VCO-01981-5 (corn, herbicide tolerance, NCIMB accession number 41842, WO2013014241A1); Event DAS-81419-2 X DAS-68416-4 (soybean, stacked insect resistance and herbicide tolerance, ATCC accession number PTA-10442, WO2013016516A1); Event DAS-81419-2 (soybean, stacked insect resistance and herbicide tolerance, ATCC accession number PTA-12006, WO2013016527A1); Event HCEM485 (corn, herbicide tolerance, ATCC accession number PTA-12014, WO2013025400A1); Event pDAB4468.18.07.1 (cotton, herbicide tolerance, ATCC accession number PTA-12456, WO2013112525A2); Event pDAB4468.19.10.3 (cotton, herbicide tolerance, ATCC accession number PTA-12457, WO2013112527A1).

The examples which follow illustrate the invention in detail.

A. CHEMICAL EXAMPLES

Example 2-5: Synthesis of 5-(trifluoromethyl)-2,3-dihydro-1,4-benzodithiine-N-(1-methyltetrazol-5-yl)-8-carboxamide

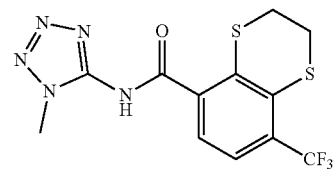 [SMILES: Cn1nnnc1NC(=O)c1ccc(C(F)(F)F)c2c1SCCS2]

At 0° C., 0.28 ml (3.9 mmol) of thionyl chloride are added dropwise to 840 mg (3 mmol) of 5-(trifluoromethyl)-2,3-dihydro-1,4-benzodithiine-7-carboxylic acid, 1.2 g (15 mmol) of 1-methyl-1H-imidazole and 450 mg (4.5 mmol) of 5-amino-1-methyltetrazole in 10 ml of acetonitrile. After 24 hours at room temperature, water and 2N hydrochloric acid are added and the mixture is diluted with ethyl acetate. The organic phase is washed with sat. sodium bicarbonate solution and sat. sodium chloride solution, dried and concentrated and the residue obtained is purified by RP-HPLC column chromatography. Yield 0.293 g (27% yield).

Intermediate 2-5A: Synthesis of methyl 5-(trifluoromethyl)-2,3-dihydro-1,4-benzodithiine-7-carboxylate A mixture of 2 g (8.3 mmol) of methyl 2,3-difluoro-4-(trifluoromethyl)benzoate, 0.84 ml (10 mmol) of ethanedithiol and 3.34 g (24 mmol) of potassium carbonate in 25 ml of DMF is stirred at RT for 20 h and at 80° C. for 2 h. The mixture is then diluted with ethyl acetate and washed with 2N hydrochloric acid (3×), sat. sodium bicarbonate solution and sat. sodium chloride solution. The org. phase is dried and concentrated. Yield 2.24 g.

Intermediate 2-5B: Synthesis of 5-(trifluoromethyl)-2,3-dihydro-1,4-benzodithiine-7-carboxylic acid 12 ml of 2N aqueous sodium hydroxide solution are added to 2.85 g (9.68 mmol) methyl 5-(trifluoro-methyl)-2,3-dihydro-1,4-benzodithiine-7-carboxylate in 30 ml of methanol, and the mixture is heated at 80° C. for 4 h. The methanol is then substantially removed on a rotary evaporator, the mixture is washed with ethyl acetate and the aqueous phase is acidified with 2N hydrochloric acid. The mixture is extracted with ethyl acetate and the organic phase is dried and concentrated. Yield 2.25 g (83% yield).

Example 2-13: Synthesis of 5-(trifluoromethyl)-2,3-dihydro-1,4-benzoxathiine-N-(1-methyltetrazol-5-yl)-8-carboxamide

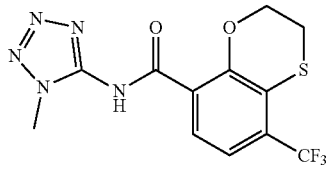 [SMILES: Cn1nnnc1NC(=O)c1ccc(C(F)(F)F)c2c1OCCS2]

1 ml (14 mmol) of thionyl chloride is added dropwise to 2.5 g (7.5 mmol, purity: 79%) of 5-(trifluoro-methyl)-2,3-dihydro-1,4-benzoxathiine-7-carboxylic acid, 2.7 g (33.6 mmol) of 1-methyl-1H-imidazole and 1.17 g (11.2 mmol) of 5-amino-1-methyltetrazole in 10 ml of acetonitrile. After 24 hours at room temperature (RT), water and 2N hydrochloric acid are added and the mixture is diluted with ethyl acetate. The organic phase is washed with sat. sodium bicarbonate solution and sat. sodium chloride solution, dried and concentrated and the residue obtained is washed with isopropyl acetate. Yield 1.65 g.

Intermediate 2-13A: Synthesis of 5-(trifluoromethyl)-2,3-dihydro-1,4-benzoxathiine-7-carboxylic acid A mixture of 3.3 g (12.2 mmol, purity: 88%) of 2-hydroxy-3-mercapto-4-(trifluoromethyl)benzoic acid, 8.7 ml (36.6 mmol) of tributylamine and 2.98 g (15.8 mmol) of 1,2-dibromoethane in 20 ml of acetonitrile is stirred at RT for 30 min and at 70° C. for 1 h. The mixture is then diluted with 10% strength aqueous sodium hydroxide solution and extracted with ethyl acetate. The aqueous phase is acidified with hydrochloric acid and extracted with ethyl acetate. The org. phase is dried and concentrated. Yield 3.15 g (purity: 79%).

Example 2-17: Synthesis of 5-(trifluoromethyl)-2,3-dihydro-1,4-benzoxathiine-N-(1-methyltetrazol-5-yl)-8-carboxamide 4-oxide

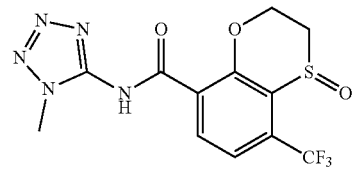 [SMILES: Cn1nnnc1NC(=O)c1ccc(C(F)(F)F)c2c1OCCS2=O]

100 mg of sulfuric acid and 0.5 ml (4.9 mmol) of hydrogen peroxide (30% strength) are added to 360 mg (1 mmol) of 5-(trifluoromethyl)-2,3-dihydro-1,4-benzoxathiine-N-(1-methyltetrazol-5-yl)-8-carboxamide in 7 ml of acetonitrile and the mixture is then heated to 50° C. until no more starting material can be detected. The mixture is then diluted with ethyl acetate and washed with sodium bisulfite solution and sat. sodium chloride solution. The dried org. phase is concentrated, a little acetonitrile is added to the residue and the crystals are filtered off with suction. Yield 314 mg.

Example 2-20: Synthesis of 5-(trifluoromethyl)-2,3-dihydro-1,4-benzoxathiine-N-(1-methyltetrazol-5-yl)-8-carboxamide 4,4-dioxide

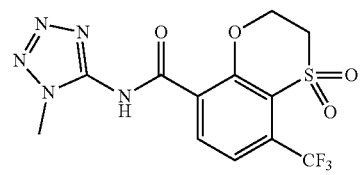 [SMILES: Cn1nnnc1NC(=O)c1ccc(C(F)(F)F)c2c1OCCS2(=O)=O]

A little at a time, 790 mg (5 mmol) of potassium permanganate are added to 410 mg (1.2 mmol) of 5-(trifluoromethyl)-2,3-dihydro-1,4-benzoxathiine-N-(1-methyltetrazol-5-yl)-8-carboxamide in a mixture of 20 ml of acetic acid and 2 ml of water. The mixture is then added to 80 ml of water and excess permanganate and manganese dioxide are reduced using sodium bisulfite solution. The mixture is extracted with ethyl acetate and the org. phase is washed with sat. sodium chloride solution, dried and concentrated. The crystals obtained are, after filtration with suction, washed with heptane. Yield 335 mg.

Example 3-13: Synthesis of 5-(trifluoromethyl)-2,3-dihydro-1,4-benzoxathiine-N-(1-ethyltetrazol-5-yl)-8-carboxamide

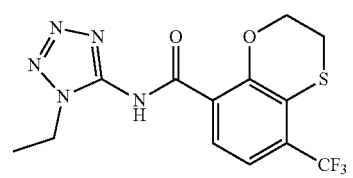 [SMILES: CCn1nnnc1NC(=O)c1ccc(C(F)(F)F)c2c1OCCS2]

0.20 ml (2.3 mmol) of oxalyl chloride is added dropwise to 600 mg (1.6 mmol, purity: 70%) of 5-(trifluoromethyl)-

2,3-dihydro-1,4-benzoxathiine-7-carboxylic acid, 1.0 g (12.5 mmol) of 1-methyl-1H-imidazole, 1.3 ml (15.9 mmol) of pyridine and 255 mg (2.2 mmol) of 5-amino-1-ethyltetrazole in 4 ml of acetonitrile. After 24 hours at RT, water and 2N hydrochloric acid are added and the mixture is diluted with ethyl acetate. The organic phase is washed with sat. sodium chloride solution, dried and concentrated and the residue obtained is filtered over a column (mobile phase: heptane/ethyl acetate: 1/1). After concentration of the product fractions, the solid obtained is washed with heptane. Yield 368 mg.

The NMR data of disclosed examples are listed either in conventional form (δ values, number of hydrogen atoms, multiplet splitting) or as so-called NMR peak lists. In the NMR peak list method, the NMR data of selected examples are recorded in the form of NMR peak lists, where for each signal peak first the δ value in ppm and then, separated by a space, the signal intensity are listed. The δ value/signal intensity number pairs for different signal peaks are listed with separation from one another by semicolons.

The peak list for one example therefore takes the form of:

$\delta_1$ (intensity$_1$); $\delta_2$ (intensity$_2$); ... ; $\delta_i$ (intensity$_i$); ... ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO.

Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of $^1$H NMR peak lists can be found in the Research Disclosure Database Number 564025.

Analytical Data (Conventional Evaluation)

| No. | NMR |
|---|---|
| 2-5 | $^1$H-NMR(400.0 MHz, DMSO-d$^6$): δ = 11.82 (br s, 1H); 7.72 (d, 1H); 7.61 (d, 1H); 4.02 (s, 3H); 3.35-3.30 (m, 4H) |
| 2-11 | $^1$H-NMR(400.0 MHz, DMSO-d$_6$): δ = 11.99 (brs, 1H); 8.52 (d, 1H); 8.36 (d, 1H); 4.58 (bd, 2H); 4.51 (bd, 2H); 4.04 (s, 3H) |
| 2-13 | $^1$H-NMR(400.0 MHz, CDCl$_3$): δ = 10.20 (br s, 1H); 7.98 (d, 1H); 7.41 (d, 1H); 4.76 (m, 2H); 4.06 (s, 3H); 3.27 (m, 2H) |
| 2-15 | $^1$H-NMR(400.0 MHz, DMSO-d$_6$): δ = 11.39 (brs, 1H); 7.52 (d, 1H); 7.34 (d, 1H); 4.53 (brs, 2H); 3.96 (s, 3H); 3.26 (m, 2H) |
| 2-16 | $^1$H-NMR(400.0 MHz, DMSO-d$_6$): δ = 11.31 (br s, 1H); 7.53 (d, 1H); 7.48 (d, 1H); 7.05 (br s, 1H); 5.60 (s, 1H); 4.49 (m, 1H); 4.31 (m, 1H); 3.97 (s, 3H) |
| 2-17 | $^1$H-NMR(400.0 MHz, DMSO-d$_6$): δ = 11.51 (br s, 1H); 8.02 (d, 1H); 7.62 (d, 1H); 4.81 (m, 2H); 3.98 (s, 3H); 3.49 (m, 1H); 3.33 (m, 1H) |
| 2-20 | $^1$H-NMR(400.0 MHz, DMSO-d$_6$): δ = 11.51 (br s, 1H); 8.04 (d, 1H); 7.71 (d, 1H); 4.91 (m, 2H); 4.02 (m, 2H); 3.97 (s, 3H) |
| 2-41 | $^1$H-NMR(400.0 MHz, DMSO-d$_6$): δ = 11.58 (br s, 1H); 7.63 (d, 1H); 7.56 (d, 1H); 6.36 (d, 1H); 4.75 (dd, H); 4.61 (d, 1H); 3.97 (s, 3H) |
| 3-13 | $^1$H-NMR(400.0 MHz, DMSO-d$_6$): δ = 11.27 (br s, 1H); 7.49 (d, 1H); 7.44 (d, 1H); 4.53 (br s, 2H); 4.33 (q, 2H); 3.29 (m, 2H); 1.45 (t, 3H) |
| 3-16 | $^1$H-NMR(400.0 MHz, DMSO-d$_6$): δ = 11.43 (br s, 1H); 8.02 (d, 1H); 7.61 (d, 1H); 4.80 (m, 2H); 4.35 (q, 2H); 3.48 (m, 1H); 3.31 (m, 1H); 1.47 (t, 3H) |
| 3-19 | $^1$H-NMR(400.0 MHz, DMSO-d$_6$): δ = 11.42 (br s, 1H); 8.04 (d, 1H); 7.71 (d, 1H); 4.92 (br s, 2H); 4.34 (q, 2H); 4.02 (br s, 2H); 1.46 (t, 3H) |
| 5-64 | $^1$H-NMR(400.0 MHz, CDCl$_3$): δ = 7.61 (dd, 1H); 7.50 (d, 1H); 3.95 (s, 3H); 3.32 (dd, 2H); 3.17 (dd, 2H) |
| 6-64 | $^1$H-NMR(400.0 MHz, DMSO-d$_6$): δ = 13.7 (brs, 1H); 7.62-7.52 (m, 2H); 3.35 (dd, 2H); 3.20 (dd, 2H) |

B. FORMULATION EXAMPLES

1. Dusting Products

A dusting product is obtained by mixing 10 parts by weight of a compound of the formula (I) and 90 parts by weight of talc as an inert substance and comminuting the mixture in a hammer mill.

2. Dispersible Powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

3. Dispersion Concentrate

A readily water-dispersible dispersion concentrate is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to more than 277° C.) and grinding the mixture in a friction ball mill to a fineness of below 5 microns.

4. Emulsifiable Concentrate

An emulsifiable concentrate is obtained from 15 parts by weight of a compound of the formula (I), 75 parts by weight of cyclohexanone as a solvent and 10 parts by weight of ethoxylated nonylphenol as an emulsifier.

5. Water-Dispersible Granules

Water-dispersible granules are obtained by mixing 75 parts by weight of a compound of the formula (I),

| | |
|---|---|
| 10 | of calcium lignosulfonate, |
| 5 | of sodium laurylsulfate, |
| 3 | of polyvinyl alcohol and |
| 7 | of kaolin, | then grinding the mixture in a pinned-disk mill, and granulating the powder in a fluidized bed by spray application of water as a granulating liquid.

Water-dispersible granules are also obtained by homogenizing and precomminuting, in a colloid mill, 25 parts by weight of a compound of the formula (I),

| | |
|---|---|
| 5 | of sodium 2,2'-dinaphthylmethane-6,6'-disulfonate, |
| 2 | of sodium oleoylmethyltaurinate, |
| 1 | of polyvinyl alcohol, |
| 17 | of calcium carbonate and |
| 50 | of water, | then grinding the mixture in a bead mill and atomizing and drying the suspension thus obtained in a spray tower by means of a one-phase nozzle.

C. BIOLOGICAL EXAMPLES

Test Description

In the tables below, the following abbreviations are used:

Undesired Plants/Weeds:

| ABUTH: | *Abutilon theophrasti* | ALOMY | *Alopecurus myosuroides* |
|---|---|---|---|
| AMARE: | *Amaranthus retroflexus* | AVEFA: | *Avena fatua* |
| CYPES: | *Cyperus esculentus* | ECHCG: | *Echinochloa crus-galli* |
| LOLMU: | *Lolium multiflorum* | MATIN: | *Matricaria inodora* |
| PHBPU: | *Ipomoea purpurea* | POLCO: | *Polygonum convolvulus* |
| SETVI: | *Setaria viridis* | STEME: | *Stellaria media* |
| VERPE: | *Veronica persica* | VIOTR: | *Viola tricolor* |

1. Pre-emergence herbicidal action and crop plant compatibility (pre-emergence, PE) Seeds of monocotyledonous and dicotyledonous weed plants and crop plants are placed in plastic or organic planting pots and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate of 600l/ha (converted). After the treatment, the pots are placed in a greenhouse and kept under good growth conditions for the trial plants. After about 3 weeks, the effect of the preparations is scored visually in comparison with untreated controls as percentages. The tables below show the herbicidal activity of numerous compounds according to the invention against important harmful plants. For example, 100% activity=the plants have died, 0% activity=like control plants.

PE

| Example Number | Application rate | AVEFA |
|---|---|---|
| 2-13 | 320 | 80 |
| 2-17 | 320 | 80 |
| 2-20 | 320 | 100 |
| 3-13 | 320 | 80 |
| 3-16 | 320 | 100 |
| 3-19 | 320 | 90 |

PE

| Example Number | Application rate | CYPES |
|---|---|---|
| 2-13 | 320 | 90 |
| 2-17 | 320 | 100 |
| 2-20 | 320 | 100 |
| 3-13 | 320 | 100 |
| 3-16 | 320 | 100 |
| 3-19 | 320 | 100 |

PE

| Example Number | Application rate | ECHCG |
|---|---|---|
| 2-13 | 320 | 100 |
| 2-17 | 320 | 100 |
| 2-20 | 320 | 100 |
| 3-13 | 320 | 100 |
| 3-16 | 320 | 100 |
| 3-19 | 320 | 100 |

PE

| Example Number | Application rate | SETVI |
|---|---|---|
| 2-13 | 320 | 100 |
| 2-17 | 320 | 100 |
| 2-20 | 320 | 100 |
| 3-13 | 320 | 100 |
| 3-16 | 320 | 100 |
| 3-19 | 320 | 100 |

PE

| Example Number | Application rate | SETVI |
|---|---|---|
| 2-5 | 80 | 90 |

PE

| Example Number | Application rate | ABUTH |
|---|---|---|
| 2-13 | 320 | 100 |
| 2-17 | 320 | 100 |
| 2-20 | 320 | 100 |
| 3-13 | 320 | 100 |
| 3-16 | 320 | 100 |
| 3-19 | 320 | 100 |

PE

| Example Number | Application rate | ABUTH |
|---|---|---|
| 2-5 | 80 | 100 |
| 2-11 | 80 | 100 |

PE

| Example Number | Application rate | AMARE |
|---|---|---|
| 2-13 | 320 | 100 |
| 2-17 | 320 | 100 |
| 2-20 | 320 | 100 |
| 3-13 | 320 | 100 |
| 3-16 | 320 | 100 |
| 3-19 | 320 | 100 |

PE

| Example Number | Application rate | AMARE |
|---|---|---|
| 2-5 | 80 | 100 |
| 2-11 | 80 | 80 |

PE

| Example Number | Application rate | MATIN |
|---|---|---|
| 2-13 | 320 | 100 |
| 2-17 | 320 | 90 |
| 2-20 | 320 | 100 |
| 3-13 | 320 | 90 |
| 3-16 | 320 | 100 |
| 3-19 | 320 | 100 |

PE

| Example Number | Application rate | MATIN |
|---|---|---|
| 2-5 | 80 | 100 |
| 2-11 | 80 | 80 |

PE

| Example Number | Application rate | POLCO |
|---|---|---|
| 2-13 | 320 | 80 |
| 2-20 | 320 | 100 |
| 3-13 | 320 | 90 |
| 3-16 | 320 | 100 |
| 3-19 | 320 | 90 |

PE

| Example Number | Application rate | STEME |
|---|---|---|
| 2-13 | 320 | 90 |
| 2-17 | 320 | 100 |

-continued

| Example Number | Application rate | STEME |
|---|---|---|
| 2-20 | 320 | 90 |
| 3-13 | 320 | 100 |
| 3-16 | 320 | 100 |
| 3-19 | 320 | 90 |

PE

| Example Number | Application rate | STEME |
|---|---|---|
| 2-5 | 80 | 90 |

PE

| Example Number | Application rate | VIOTR |
|---|---|---|
| 2-13 | 320 | 100 |
| 2-17 | 320 | 100 |
| 2-20 | 320 | 100 |
| 3-13 | 320 | 100 |
| 3-16 | 320 | 100 |
| 3-19 | 320 | 100 |

PE

| Example Number | Application rate | VIOTR |
|---|---|---|
| 2-5 | 80 | 100 |
| 2-13 | 320 | 100 |
| 2-17 | 320 | 100 |
| 2-20 | 320 | 100 |

PE
PE

| Example Number | Application rate | VERPE |
|---|---|---|
| 2-5 | 80 | 90 |

In a comparative experiment, by way of example, the herbicidal activity of compound No. 2-13 according to the invention was compared to that of compound No. A-117 known from WO 2013/076315 A2. Here, the superiority of the compound according to the invention was demonstrated clearly on the basis of numerous harmful plants:

| Example No. | Dosage [g/ha] | Herbicidal action against | | | | |
|---|---|---|---|---|---|---|
| | | SETVI | ALOMY | AVEFA | ABUTH | MATIN |
| 2-13 | 320 | 100% | 90% | 80% | 100% | 100% |
| A-117 | 320 | 0% | 0% | 0% | 0% | 30% |

2. Post-emergence herbicidal action and crop plant compatibility (post-emergence, PO) Seeds of monocotyledonous and dicotyledonous weeds and crop plants are placed in sandy loam in plastic or organic planting pots, covered with soil and cultivated in a greenhouse under controlled growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion with addition of 0.5% additive at a water application rate of 6001/ha (converted). After the test plants had been kept in the greenhouse under optimum growth conditions for about 3 weeks, the activity of the preparations is rated visually in comparison to untreated controls. The tables below show the herbicidal activity of numerous compounds according to the invention against important harmful plants. For example, 100% activity=the plants have died, 0% activity=like control plants.

PO

| Example Number | Application rate | ALOMY |
|---|---|---|
| 2-13 | 80 | 90 |
| 2-17 | 80 | 90 |
| 2-20 | 80 | 80 |

PO

| Example Number | Application rate | AVEFA |
|---|---|---|
| 2-13 | 80 | 90 |
| 2-17 | 80 | 100 |
| 2-20 | 80 | 80 |
| 3-13 | 80 | 90 |
| 3-16 | 80 | 100 |

PO

| Example Number | Application rate | CYPES |
|---|---|---|
| 2-17 | 80 | 100 |
| 2-20 | 80 | 80 |
| 3-16 | 80 | 90 |
| 3-19 | 80 | 80 |

PO

| Example Number | Application rate | ECHCG |
|---|---|---|
| 2-11 | 80 | 80 |
| 2-13 | 80 | 90 |
| 2-17 | 80 | 90 |
| 2-20 | 80 | 90 |
| 3-13 | 80 | 100 |
| 3-16 | 80 | 90 |
| 3-19 | 80 | 100 |

PO

| Example Number | Application rate | ECHCG |
|---|---|---|
| 2-5 | 20 | 90 |

PO

| Example Number | Application rate | LOLMU |
|---|---|---|
| 2-13 | 80 | 80 |
| 2-17 | 80 | 90 |
| 2-20 | 80 | 80 |

PO

| Example Number | Application rate | SETVI |
|---|---|---|
| 2-13 | 80 | 90 |
| 2-17 | 80 | 90 |
| 2-20 | 80 | 90 |
| 3-13 | 80 | 90 |
| 3-16 | 80 | 90 |
| 3-19 | 80 | 90 |

PO

| Example Number | Application rate | ABUTH |
|---|---|---|
| 2-13 | 80 | 100 |
| 2-17 | 80 | 100 |
| 2-20 | 80 | 100 |
| 3-13 | 80 | 100 |
| 3-16 | 80 | 100 |
| 3-19 | 80 | 90 |

PO

| Example Number | Application rate | ABUTH |
|---|---|---|
| 2-5 | 20 | 90 |

PO

| Example Number | Application rate | AMARE |
|---|---|---|
| 2-13 | 80 | 90 |
| 2-17 | 80 | 90 |
| 2-20 | 80 | 100 |
| 3-13 | 80 | 90 |
| 3-16 | 80 | 100 |
| 3-19 | 80 | 90 |

PO

| Example Number | Application rate | AMARE |
|---|---|---|
| 2-5 | 20 | 100 |
| 2-41 | 80 | 90 |

PO

| Example Number | Application rate | MATIN |
|---|---|---|
| 2-13 | 80 | 90 |
| 2-17 | 80 | 90 |
| 2-20 | 80 | 100 |

PO

| Example Number | Application rate | PHBPU |
|---|---|---|
| 2-13 | 80 | 90 |
| 2-17 | 80 | 100 |
| 2-20 | 80 | 90 |
| 3-13 | 80 | 90 |
| 3-16 | 80 | 100 |
| 3-19 | 80 | 90 |

PO

| Example Number | Application rate | POLCO |
|---|---|---|
| 2-13 | 80 | 80 |
| 2-17 | 80 | 90 |
| 2-20 | 80 | 100 |
| 3-13 | 80 | 100 |
| 3-16 | 80 | 90 |

PO

| Example Number | Application rate | STEME |
|---|---|---|
| 2-17 | 80 | 100 |
| 2-13 | 80 | 90 |
| 2-20 | 80 | 90 |
| 3-13 | 80 | 100 |
| 3-16 | 80 | 100 |
| 3-19 | 80 | 100 |

PO

| Example Number | Application rate | STEME |
|---|---|---|
| 2-5 | 20 | 80 |

PO

| Example Number | Application rate | VIOTR |
|---|---|---|
| 2-11 | 80 | 90 |
| 2-13 | 80 | 100 |
| 2-17 | 80 | 100 |
| 2-20 | 80 | 100 |
| 3-13 | 80 | 100 |
| 3-16 | 80 | 100 |
| 3-19 | 80 | 100 |

PO

| Example Number | Application rate | VIOTR |
|---|---|---|
| 2-5 | 20 | 80 |

PO

| Example Number | Application rate | VERPE |
|---|---|---|
| 2-11 | 80 | 80 |
| 2-13 | 80 | 100 |
| 2-17 | 80 | 100 |
| 2-20 | 80 | 100 |
| 3-16 | 80 | 100 |

In a comparative experiment, by way of example, the herbicidal activity of compound No. 2-13 according to the invention was compared to that of compound No. A-117 known from WO 2013/076315 A2. Here, the superiority of the compound according to the invention was demonstrated clearly on the basis of numerous harmful plants.

| | Dosage | Herbicidal action against | | | | |
|---|---|---|---|---|---|---|
| Example No. | [g/ha] | LOLMU | ALOMY | AVEFA | ABUTH | POLCO |
| 2-13 | 80 | 80% | 90% | 90% | 100% | 80% |
| A-117 | 80 | 0% | 20% | 0% | 50% | 10% |

The invention claimed is:

1. A compound of formula (I) and/or an agrochemically acceptable salt thereof, in which the symbols and indices have the following meanings:

(I)

B represents N or CH,
$X^1$, $X^2$ independently of one another each represent O or $S(O)_n$,
R represents halo-$(C_1-C_6)$-alkyl,
$R^a$, $R^b$, $R^c$, $R^d$ independently of one another each represent hydrogen, fluorine, chlorine, hydroxy, $(C_1-C_6)$-alkyl, halo-$(C_1-C_6)$-alkyl, $(C_1-C_6)$-alkyloxy, $(C_1-C_6)$-alkylthio, cyano, or
$R^a$ and $R^b$ or $R^c$ and $R^d$ together represent an oxo or a thiooxo group,
$R^x$ represents $(C_1-C_6)$-alkyl, $(C_1-C_6)$-alkyl-O—$(C_1-C_6)$-alkyl, phenyl,
n represents 0, 1 or 2.

2. The compound as claimed in claim 1, in which
B represents N or CH,
$X^1$, $X^2$ independently of one another each represent O or $S(O)_n$,
R represents halo-$(C_1-C_3)$-alkyl, $R^a$, $R^b$, $R^c$, $R^d$ independently of one another each represent hydrogen, fluorine, chlorine, hydroxy, ($C_1$-$C_6$)-alkyl, halo-($C_1$-$C_6$)-alkyl, ($C_1$-$C_6$)-alkyloxy, ($C_1$-$C_6$)-alkylthio, cyano, or $R^a$ and $R^b$ or $R^c$ and $R^d$ together represent an oxo or a thiooxo group, $R^x$ represents ($C_1$-$C_3$)-alkyl, ($C_1$-$C_3$)-alkyl-O—($C_1$-$C_3$)-alkyl, phenyl, n represents 0, 1 or 2.

3. The compound as claimed in claim 1, in which

B represents N or CH, $X^1$, $X^2$ independently of one another each represent O or $S(O)_n$, R represents trifluoromethyl, difluoromethyl or pentafluoroethyl, $R^a$, $R^b$, $R^c$, $R^d$ independently of one another each represent hydrogen, fluorine, chlorine, hydroxy, methyl, ethyl, trifluoromethyl, difluoromethyl, methoxy, ethoxy, methylthio, ethylthio, cyano, or $R^a$ and $R^b$ or $R^c$ and $R^d$ together represent an oxo or a thiooxo group, $R^x$ represents methyl, ethyl, propyl, methoxymethyl, methoxyethyl, 2-methoxy-2-methyl-1-propyl, phenyl, n represents 0, 1 or 2.

4. An herbicidal composition comprising at least one compound as claimed in claim 1 mixed with one or more formulation auxiliaries.

5. The herbicidal composition as claimed in claim 4, comprising at least one further pesticidally active substance selected from the group consisting of insecticides, acaricides, herbicides, fungicides, safeners, and growth regulators.

6. A method for controlling one or more unwanted plants, comprising applying an effective amount of at least one compound as claimed in claim 1 or an herbicidal composition thereof to the plants and/or to a site of unwanted vegetation.

7. A product comprising one or more compounds as claimed in claim 1 for controlling one or more unwanted plants.

8. The product as claimed in claim 7, wherein the compound is used for controlling one or more unwanted plants in one or more crops of useful plants.

9. The product as claimed in claim 8, wherein the useful plants are transgenic useful plants.

* * * * *

UNITED STATES PATENT AND TRADEMARK OFFICE
CERTIFICATE OF CORRECTION

PATENT NO. : 12,286,425 B2
APPLICATION NO. : 16/975642
DATED : April 29, 2025
INVENTOR(S) : Memmel et al.

Page 1 of 5

It is certified that error appears in the above-identified patent and that said Letters Patent is hereby corrected as shown below:

On the Title Page

In Item (72), under "Inventors", in Column 1, Line 10, delete "Hofheim" and insert -- Hösbach --, therefor.

In Item (57), under "ABSTRACT", in Column 2, Line 6, delete "IV" and insert -- $R^x$ --, therefor.

In the Specification

In Column 4, Line 13, delete "$C_6$)-alkyl," and insert -- ($C_1$-$C_6$)-alkyl, --, therefor.

In Column 5, Line 14, delete "thiooxyl" and insert -- thiooxo --, therefor.

In Column 6, Line 16, delete "formula (I)" and insert -- formula (II) --, therefor.

In Columns 13 & 14, in TABLE 4, under "$X^2$", Line 12, delete "5" and insert -- S --, therefor.

In Columns 15 & 16, in TABLE 5, Line 3, delete " 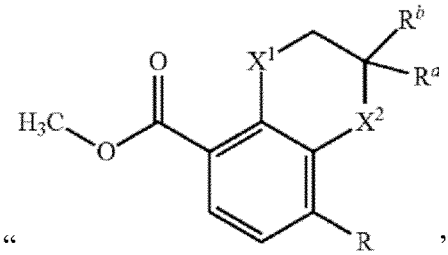 " and insert

Signed and Sealed this
Twenty-seventh Day of January, 2026

John A. Squires
*Director of the United States Patent and Trademark Office*

-- 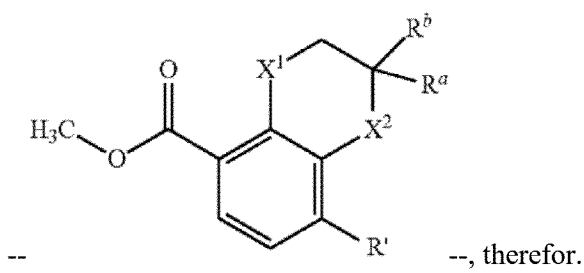 --, therefor.
In Columns 17 & 18, in TABLE 5-continued, Line 3, delete " 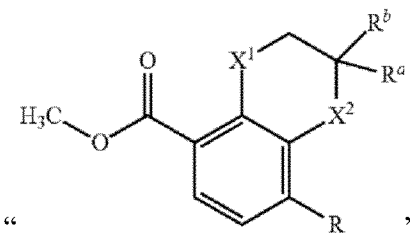 " and insert -- 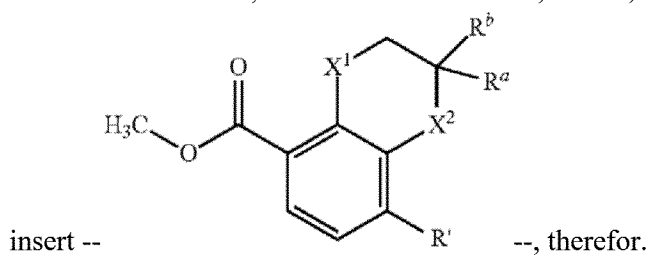 --, therefor.
In Columns 17 & 18, in TABLE 6, Line 3, delete " 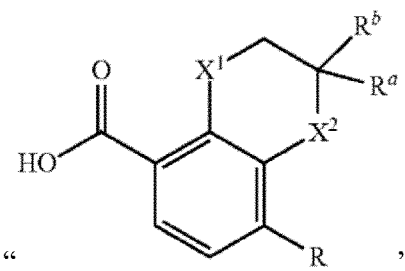 " and insert -- 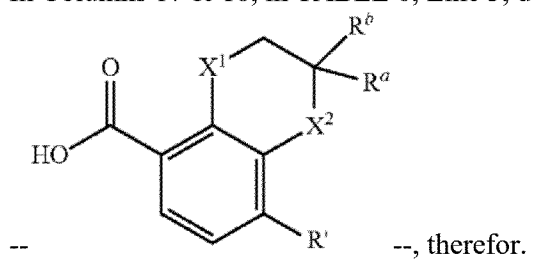 --, therefor.

In Columns 19 & 20, in TABLE 6-continued, Line 3, delete " 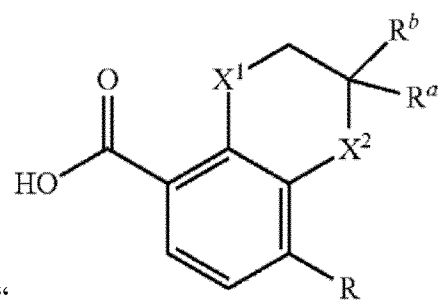 "

and insert -- 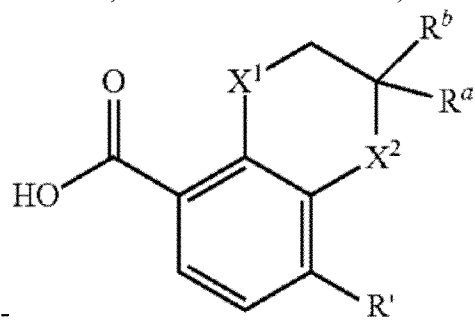 --, therefor.

In Columns 21 & 22, in TABLE 7, Line 3, delete " 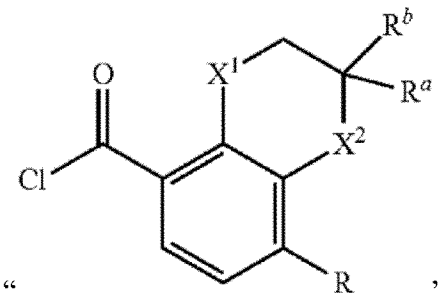 " and insert -- 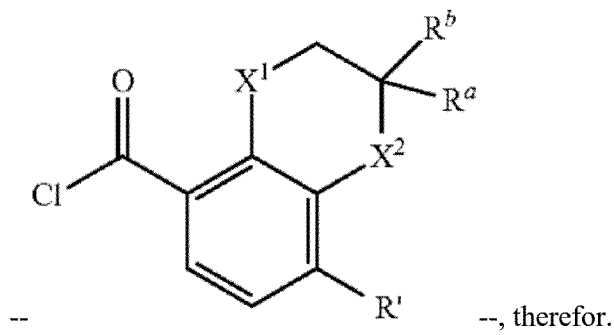 --, therefor.

In Column 23, Line 25, delete "S(O)," and insert -- $S(O)_n$, -- therefor.

In Column 24, Line 30, delete "X" and insert -- $X^1$ --, therefor.

In Column 28, Line 14, delete "formula (as" and insert -- formula (I) as --, therefor.

In Column 29, Line 30, delete "bicyclopyron," and insert -- bicyclopyrone, --, therefor.

CERTIFICATE OF CORRECTION (continued)
U.S. Pat. No. 12,286,425 B2

In Column 29, Line 47, delete "-diolamin," and insert -- -diolamine, --, therefor.

In Column 30, Lines 18-19, delete "0-(2,4-dimethyl-6-nitrophenyl)O-ethyl" and insert -- O-(2,4-dimethyl-6-nitrophenyl) O-ethyl --, therefor.

In Column 30, Line 54, delete "oxaziclomefon," and insert -- oxaziclomefone, --, therefor.

In Column 32, Line 12, delete "prohydrojasmone," and insert -- prohydrojasmon, --, therefor.

In Column 33, Line 6, delete "(S)" and insert -- (S1) --, therefor.

In Column 35, Line 12, delete "$R^c$" and insert -- $R_C^1$ --, therefor.

In Column 36, Line 4, delete "NHCO—$R_D^1$;" and insert -- NHCO-$R_D^7$; --, therefor.

In Column 36, Line 45, delete "(S4a)" and insert -- ($S4^a$) --, therefor.

In Column 37, Line 24, delete "($S4^b$)," and insert -- ($S4^c$), --, therefor.

In Column 37, Line 49, delete "(S4)," and insert -- ($S4^d$), --, therefor.

In Column 39, Lines 5-6, delete "($C_1$-$C_4$)-alkenyl, ($C_1$-$C_4$)-alkynyl" and insert -- ($C_2$-$C_4$)-alkenyl, ($C_2$-$C_4$)-alkynyl --, therefor.

In Column 39, Line 31, delete "(S10a)" and insert -- ($S10^a$) --, therefor.

In Column 40, Line 18, delete "(13-1)," and insert -- (S13-1), --, therefor.

In Column 40, Line 21, delete "(13-2)," and insert -- (S13-2), --, therefor.

In Column 40, Lines 41-42, delete "(0,0-diethyl S-2-ethylthioethylphosphorodithioate)" and insert -- (O,O-diethyl S-2-ethylthioethyl phosphorodithioate) --, therefor.

In Column 40, Line 43, delete "(0,0-diethyl 0-phenyl phosphorothioate)" and insert -- (O,O-diethyl O-phenyl phosphorothioate) --, therefor.

In Column 41, Line 19, delete "($C_1$-$C_6$)-alkyl," and insert -- ($C_1$-$C_{16}$)-alkyl, --, therefor.

In Column 41, Line 26, delete "($C_3$—C)-cycloalkyl" and insert -- ($C_3$-$C_6$)-cycloalkyl --, therefor.

In Column 42, Lines 11-12, delete "poly glycolethersulfates," and insert -- polyglycolethersulfates, --, therefor.

CERTIFICATE OF CORRECTION (continued)
U.S. Pat. No. 12,286,425 B2

In Column 46, Line 66, delete "tristryrylphenol" and insert -- tristyrylphenol --, therefor.

In Column 47, Line 62, delete "Actinidaceae" and insert -- Actinidiaceae --, therefor.

In Column 47, Line 64, delete "Sterculiceae" and insert -- Sterculiaceae --, therefor.

In Column 56, Line 12, delete "$-1,3-glucanase" and insert -- β-1,3-glucanase --, therefor.

In Column 59, Line 17, delete "SYHTOH2/SYN-00H2-5" and insert -- SYHT0H2/SYN-00H2-5 --, therefor.

In Column 60, Line 2, delete "SYHTOH2" and insert -- SYHT0H2 --, therefor.

In Column 63, Line 14, delete "(6 values," and insert -- (δ values, --, therefor.

In Column 63, Line 18, delete "6" and insert -- δ --, therefor.

In Column 63, Line 19, delete "6" and insert -- δ --, therefor.

In Column 63, Lines 24-25, delete "$\delta_1$ (intensity$_1$); $\delta_2$ (intensity$_2$); . . . ; $\delta_1$ (intensity$_1$); . . . ; $\delta_n$ (intensity$_n$)" and insert -- $\delta_1$ (intensity$_1$); $\delta_2$ (intensity$_2$); . . . ; $\delta_i$ (intensity$_i$); . . . ; $\delta_n$ (intensity$_n$) --, therefor.

In Column 64, Line 5, delete "DMSO-d$^6$):" and insert -- DMSO-d$_6$): --, therefor.